US010407725B2

(12) United States Patent
Hakonarson et al.

(10) Patent No.: US 10,407,725 B2
(45) Date of Patent: Sep. 10, 2019

(54) METHODS OF TREATING AUTOIMMUNE CONDITIONS IN PATIENTS WITH GENETIC VARIATIONS IN DCR3 OR IN A DCR3 NETWORK GENE

(71) Applicant: The Children's Hospital of Philadelphia, Philadelphia, PA (US)

(72) Inventors: Hakon Hakonarson, Malvern, PA (US); Charlly Kao, Philadelphia, PA (US); Christopher Cardinale, Philadelphia, PA (US); Rahul Pandey, Philadelphia, PA (US); Yun Rose Li, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 15/242,210

(22) Filed: Aug. 19, 2016

(65) Prior Publication Data
US 2017/0051352 A1 Feb. 23, 2017

Related U.S. Application Data

(60) Provisional application No. 62/208,383, filed on Aug. 21, 2015, provisional application No. 62/320,400, filed on Apr. 8, 2016.

(51) Int. Cl.
*C07H 21/04* (2006.01)
*C12Q 1/68* (2018.01)
*C12Q 1/6883* (2018.01)

(52) U.S. Cl.
CPC ..... *C12Q 1/6883* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 2010/0144903 A1 | 6/2010 | Taylor et al. | |
|---|---|---|---|
| 2010/0190162 A1 | 7/2010 | Roller et al. | |
| 2011/0177502 A1* | 7/2011 | Hakonarson | C12Q 1/6883 435/6.11 |
| 2013/0315913 A1* | 11/2013 | Zhang | C07K 16/2875 424/139.1 |

FOREIGN PATENT DOCUMENTS

| WO | 2008027338 A2 | 3/2008 |
|---|---|---|
| WO | 2015010744 | 7/2011 |
| WO | 2012161856 A1 | 11/2012 |
| WO | 2014186750 A1 | 11/2014 |

OTHER PUBLICATIONS

Cardinale et al. (Genets and Immunity, vol. 14, pp. 447-452, 2013) (Year: 2013).*
Cardinale et al. Targeted resequencing identifies defective variants of decoy receptor 3 in pediatric-onset inflammatory bowel disease. Genes Immunol. (2013) 14(7):447-52.
Ordas et al. Anti-TNF monoclonal antibodies in inflammatory bowel disease: pharmacokinetics-based dosing paradigms. Clin Pharmacol Ther. (2012) 91(4):635-46.
International Search Report issued in PCT/US16/47872, dated Dec. 20, 2016.
International Search Report issued in PCT/US16/47857, dated Dec. 29, 2016.
Chadha, Sapna et al., "Haplotype structure of TNFRSF5-TNFS5F (CD40-CD40L) and association analysis in systemic lupus erythematosus", European Journal of Human Genetics, 13: 669-676 (2005).
Gagneux, Pascal et al., "Genetic Differences between Humans and Great Apes", Molecular Phylogenetics and Evolution, 18(1): 2-13 (2001).
Garcia-Bermudez, Mercedes et al., "Study of Association of CD40-CD154 Gene Polymorphisms with Disease Susceptibility and Cardiovascular Risk in Spanish Rheumatoid Arthritis Patients", PLOS One, 7(11): e49214 (2012).
Halushka, Marc K. et al., "Patterns of single-nucleotide polymorphisms in candidate genes for blood-pressure homeostasis", Nature Genetics, 22: 239-247 (1999).
Hattersley, Andrew T. et al., "Genetic Epidemiology 5, What makes a good genetic association study", The Lancet, 366: 1315-1323 (2005).
Hirschhorn, Joel N. et al., "A comprehensive review of genetic association studies", Genet. Med., 4(2): 45-61 (2002).
Li, Yun R. et al., "Meta-analysis of shared genetic architecture across ten pediatric autoimmune diseases", Nature Medicine, 21(9): 1018-1026 (2015).
Mukhopadhyay, Somnath et al., "Matrix metalloproteinase-12 is a therapeutic target for asthma in children and young adults", J. Allergy Clin. Immunol., 126: 70-76 (2010).
Onouchi, Yoshihiro et al., "CD40 ligand gene and Kawasaki disease", European Journal of Human Genetics, 12: 1062-1068 (2004).
ClinicalTrials.gov NCT02804763, NIH, National Library of Medicine, first posted Jun. 17, 2016.
Csongei, Veronika et al., "Interaction of the major inflammatory bowel disease susceptibility alleles in Crohn's disease patients", World J. Gastroenterol., 16(2): 176-183 (2010).

(Continued)

*Primary Examiner* — Jeanine A Goldberg
(74) *Attorney, Agent, or Firm* — Kathleen D. Rigaut; Howson & Howson LLP

(57) ABSTRACT

The present disclosure relates to methods of treating autoimmune conditions in patients who have genetic alterations in the TNFRSF6B gene, which codes for the decoy receptor 3 protein (DcR3), for example that reduce the expression, secretion, or ligand binding activity of DcR3. For example, in some embodiments, the conditions may be treated with molecules that inhibit the activity of DcR3 ligands such as LIGHT, TL1A, and FasL, such as anti-LIGHT, anti-TL1A, and anti-FasL antibodies, or inhibitors of the non-canonical NF-κB pathway.

16 Claims, 6 Drawing Sheets

Specification includes a Sequence Listing.

(56) References Cited

OTHER PUBLICATIONS

Duerr, Richard H. et al., "A Genome-Wide Association Study Identifies IL23R as an Inflammatory Bowel Disease Gene", Science, 314: 1461-1463 (2006).

Hinks, Anne et al., "Association Between the PTPN22 Gene and Rheumatoid Arthritis and Juvenile Idiopathic Arthritis in a UK Population", Arthritis & Rheumatism, 52(6): 1694-1699 (2005).

Li, Yi et al., "The Association Between Interleukin-23 Receptor Gene Polymorphisms and Systemic Lupus Erythemnatosus", DNA and Cell Biology, 29(2): 79-82 (2010).

Partial Supplementary European Search Report issued in corresponding European Patent Application No. 16839901.2, dated Oct. 31, 2018.

Franchimont, N. et al., "Increased expression of receptor activator of NF-kappaB ligand (RANKL), its receptor RANK and its decoy receptor osteoprotegerin in the colon of Crohn's disease patients", Clinical and Experimental Immunology, 138(3): 491-498 (2004).

Kugathasan et al., "Loci on 20q13 and 21q22 are associated with pediatric-onset inflammatory bowel disease", Nature Genet., 40(10): 1211-1215 (2008.

Cheung et al., "Polymorphic Variants of Light (TNF Superfamily-14) Alter Receptor Avidity and Bioavailability", The Journal of Immunology, 185(3): 1949-1958 (2010).

Extended European Search Report, dated Dec. 5, 2018, issued in corresponding European Application No. 16839906.1.

\* cited by examiner

SEQUENCE LISTING

<160> NUMBER OF SEQ ID NOS: 87

<210> SEQ ID NO 1
<211> LENGTH: 300
<212> TYPE: PRT
<213> ORGANISM: Homo Sapiens

<400> SEQUENCE: 1

```
Met Arg Ala Leu Glu Gly Pro Gly Leu Ser Leu Leu Cys Leu Val Leu
1               5                   10                  15

Ala Leu Pro Ala Leu Leu Pro Val Pro Ala Val Arg Gly Val Ala Glu
                20                  25                  30

Thr Pro Thr Tyr Pro Trp Arg Asp Ala Glu Thr Gly Glu Arg Leu Val
            35                  40                  45

Cys Ala Gln Cys Pro Pro Gly Thr Phe Val Gln Arg Pro Cys Arg Arg
        50                  55                  60

Asp Ser Pro Thr Thr Cys Gly Pro Cys Pro Pro Arg His Tyr Thr Gln
65                  70                  75                  80

Phe Trp Asn Tyr Leu Glu Arg Cys Arg Tyr Cys Asn Val Leu Cys Gly
                85                  90                  95

Glu Arg Glu Glu Glu Ala Arg Ala Cys His Ala Thr His Asn Arg Ala
                100                 105                 110

Cys Arg Cys Arg Thr Gly Phe Phe Ala His Ala Gly Phe Cys Leu Glu
            115                 120                 125
```

-continued

His Ala Ser Cys Pro Pro Gly Ala Gly Val Ile Ala Pro Gly Thr Pro
    130                 135                 140

Ser Gln Asn Thr Gln Cys Gln Pro Cys Pro Pro Gly Thr Phe Ser Ala
145                 150                 155                 160

Ser Ser Ser Ser Glu Gln Cys Gln Pro His Arg Asn Cys Thr Ala
            165                 170                 175

Leu Gly Leu Ala Leu Asn Val Pro Gly Ser Ser Ser His Asp Thr Leu
            180                 185                 190

Cys Thr Ser Cys Thr Gly Phe Pro Leu Ser Thr Arg Val Pro Gly Ala
        195                 200                 205

Glu Glu Cys Glu Arg Ala Val Ile Asp Phe Val Ala Phe Gln Asp Ile
210                 215                 220

Ser Ile Lys Arg Leu Gln Arg Leu Leu Gln Ala Leu Glu Ala Pro Glu
225                 230                 235                 240

Gly Trp Gly Pro Thr Pro Arg Ala Gly Arg Ala Ala Leu Gln Leu Lys
                245                 250                 255

Leu Arg Arg Arg Leu Thr Glu Leu Leu Gly Ala Gln Asp Gly Ala Leu
            260                 265                 270

Leu Val Arg Leu Leu Gln Ala Leu Arg Val Ala Arg Met Pro Gly Leu
        275                 280                 285

Glu Arg Ser Val Arg Glu Arg Phe Leu Pro Val His
290                 295                 300

<210> SEQ ID NO 2
<211> LENGTH: 5
<212> TYPE: PRT
<213> ORGANISM: Artificial Sequence
<220> FEATURE:
<223> OTHER INFORMATION: Heavy Chain (HC) CDR1 antibody F19

<400> SEQUENCE: 2

Gly Tyr Asn Trp His
1               5

<210> SEQ ID NO 3
<211> LENGTH: 16
<212> TYPE: PRT
<213> ORGANISM: Artificial Sequence
<220> FEATURE:
<223> OTHER INFORMATION: HC CDR2 antibody F19

<400> SEQUENCE: 3

Glu Ile Thr His Ser Gly Ser Thr Asn Tyr Asn Pro Ser Leu Lys Ser
1               5                   10                  15

<210> SEQ ID NO 4
<211> LENGTH: 14
<212> TYPE: PRT
<213> ORGANISM: Artificial Sequence
<220> FEATURE:
<223> OTHER INFORMATION: HC CDR3 antibody F19

<400> SEQUENCE: 4

Glu Ile Ala Val Ala Gly Thr Gly Tyr Tyr Gly Met Asp Val
1               5                   10

<210> SEQ ID NO 5
<211> LENGTH: 11
<212> TYPE: PRT
<213> ORGANISM: Artificial Sequence
<220> FEATURE:
<223> OTHER INFORMATION: LC CDR1 antibody F19

```
<400> SEQUENCE: 5

Arg Ala Ser Gln Gly Ile Asn Ser Ala Phe Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: LC CDR2 antibody F19

<400> SEQUENCE: 6

Asp Ala Ser Ser Leu Glu Ser
1               5

<210> SEQ ID NO 7
<211> LENGTH: 9
<212> TYPE: PRT
<213> ORGANISM: Artificial Sequence
<220> FEATURE:
<223> OTHER INFORMATION: LC CDR3 antibody F19

<400> SEQUENCE: 7

Gln Gln Phe Asn Ser Tyr Pro Leu Thr
1               5

<210> SEQ ID NO 8
<211> LENGTH: 448
<212> TYPE: PRT
<213> ORGANISM: Artificial Sequence
<220> FEATURE:
<223> OTHER INFORMATION: Heavy chain variable region antibody F19

<400> SEQUENCE: 8

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Asn Trp His Trp Ile Arg Gln Pro Pro Gly Lys Gly Leu Glu Trp Ile
        35                  40                  45

Gly Glu Ile Thr His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Arg Glu Ile Ala Val Ala Gly Thr Gly Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
```

```
                195                 200                 205
His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Glu Gly Gly Pro
225                 230                 235                 240

Ser Val Phe Leu Phe Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

<210> SEQ ID NO 9
<211> LENGTH: 214
<212> TYPE: PRT
<213> ORGANISM: Artificial Sequence
<220> FEATURE:
<223> OTHER INFORMATION: Light chain variable region antibody F19

<400> SEQUENCE: 9

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Ala
                20                  25                  30

Phe Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
                  115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 10
<211> LENGTH: 11
<212> TYPE: PRT
<213> ORGANISM: Artificial Sequence
<220> FEATURE:
<223> OTHER INFORMATION: Alternative LC CDR1 antibody F19

<400> SEQUENCE: 10

Arg Ala Ser Arg Gly Ile Asn Ser Ala Phe Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Alternative LC CDR2 antibody F19

<400> SEQUENCE: 11

Asp Ala Ser Ser Leu Glu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Alternative LC CDR3 antibody F19

<400> SEQUENCE: 12

Gln Gln Phe Asn Ser Tyr Pro Leu Thr
1               5

<210> SEQ ID NO 13
<211> LENGTH: 11
<212> TYPE: PRT
<213> ORGANISM: Artificial Sequence
<220> FEATURE:
<223> OTHER INFORMATION: Alternative LC CDR1 antibody F19

<400> SEQUENCE: 13

Arg Val Ser Gln Gly Ile Ser Ser Tyr Leu Asn
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Alternative LC CDR2 antibody F19
```

```
<400> SEQUENCE: 14

Ser Ala Ser Asn Leu Gln Ser
1               5

<210> SEQ ID NO 15
<211> LENGTH: 8
<212> TYPE: PRT
<213> ORGANISM: Artificial Sequence
<220> FEATURE:
<223> OTHER INFORMATION: Alternative LC CDR3 antibody F19

<400> SEQUENCE: 15

Ala Arg Thr Asn Ala Pro Pro Thr
1               5

<210> SEQ ID NO 16
<211> LENGTH: 11
<212> TYPE: PRT
<213> ORGANISM: Artificial Sequence
<220> FEATURE:
<223> OTHER INFORMATION: Alternative LC CDR1 antibody F19

<400> SEQUENCE: 16

Arg Met Ser Gln Gly Ile Ser Ser Tyr Leu Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Alternative LC CDR2 antibody F19

<400> SEQUENCE: 17

Ala Ala Ser Thr Leu Gln Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Alternative LC CDR3 antibody F19

<400> SEQUENCE: 18

Gln Gln Tyr Tyr Ser Phe Pro Tyr Thr
1               5

<210> SEQ ID NO 19
<211> LENGTH: 11
<212> TYPE: PRT
<213> ORGANISM: Artificial Sequence
<220> FEATURE:
<223> OTHER INFORMATION: Alternative LC CDR1 antibody F19

<400> SEQUENCE: 19

Arg Ala Ser Gln Gly Val Ser Ser Tyr Leu Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Alternative LC CDR2 antibody F19
```

<400> SEQUENCE: 20

Asp Ala Ser Asn Arg Ala Thr
1               5

<210> SEQ ID NO 21
<211> LENGTH: 8
<212> TYPE: PRT
<213> ORGANISM: Artificial Sequence
<220> FEATURE:
<223> OTHER INFORMATION: Alternative LC CDR3 antibody F19

<400> SEQUENCE: 21

Gln Gln Arg Ser Asn Trp His Pro
1               5

<210> SEQ ID NO 22
<211> LENGTH: 5
<212> TYPE: PRT
<213> ORGANISM: Artificial Sequence
<220> FEATURE:
<223> OTHER INFORMATION: HC CDR1 antibody E1

<400> SEQUENCE: 22

Arg Phe Asn Met Asn
1               5

<210> SEQ ID NO 23
<211> LENGTH: 17
<212> TYPE: PRT
<213> ORGANISM: Artificial Sequence
<220> FEATURE:
<223> OTHER INFORMATION: HC CDR2 antibody E1

<400> SEQUENCE: 23

Tyr Ile Ser Ser Ser Ser Tyr Thr Ile Tyr Tyr Ala Asp Ser Val Lys
1               5                   10                  15

Gly

<210> SEQ ID NO 24
<211> LENGTH: 7
<212> TYPE: PRT
<213> ORGANISM: Artificial Sequence
<220> FEATURE:
<223> OTHER INFORMATION: HC CDR3 antibody E1

<400> SEQUENCE: 24

Ser Ile Ala Ala Phe Asp Tyr
1               5

<210> SEQ ID NO 25
<211> LENGTH: 11
<212> TYPE: PRT
<213> ORGANISM: Artificial Sequence
<220> FEATURE:
<223> OTHER INFORMATION: LC CDR1 antibody E1

<400> SEQUENCE: 25

Arg Ala Ser Gln Gly Ile Ser Ser Ala Leu Ala
1               5                   10

<210> SEQ ID NO 26
<211> LENGTH: 7
<212> TYPE: PRT
<213> ORGANISM: Artificial Sequence
<220> FEATURE:
<223> OTHER INFORMATION: LC CDR2 antibody E1

```
<400> SEQUENCE: 26

Asp Ala Ser Ser Leu Glu Ser
1               5

<210> SEQ ID NO 27
<211> LENGTH: 8
<212> TYPE: PRT
<213> ORGANISM: Artificial Sequence
<220> FEATURE:
<223> OTHER INFORMATION: LC CDR3 antibody E1

<400> SEQUENCE: 27

Gln Gln Phe Asn Ser Tyr Arg Thr
1               5

<210> SEQ ID NO 28
<211> LENGTH: 12
<212> TYPE: PRT
<213> ORGANISM: Artificial Sequence
<220> FEATURE:
<223> OTHER INFORMATION: Alternative LC CDR1 antibody E1

<400> SEQUENCE: 28

Arg Ala Ser Gln Ser Val Ser Ser Ser Tyr Leu Thr
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Alternative LC CDR2 antibody E1

<400> SEQUENCE: 29

Gly Ala Ser Ser Arg Ala Thr
1               5

<210> SEQ ID NO 30
<211> LENGTH: 9
<212> TYPE: PRT
<213> ORGANISM: Artificial Sequence
<220> FEATURE:
<223> OTHER INFORMATION: Alternative LC CDR3 antibody E1

<400> SEQUENCE: 30

Gln Gln Tyr Gly Ser Ser Met Tyr Thr
1               5

<210> SEQ ID NO 31
<211> LENGTH: 12
<212> TYPE: PRT
<213> ORGANISM: Artificial Sequence
<220> FEATURE:
<223> OTHER INFORMATION: Alternative LC CDR1 antibody E1

<400> SEQUENCE: 31

Arg Ala Ser Gln Ser Val Ser Ser Ser Tyr Leu Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Alternative LC CDR2 antibody E1
```

<400> SEQUENCE: 32

Gly Ala Ser Asn Arg Ala Thr
1               5

<210> SEQ ID NO 33
<211> LENGTH: 9
<212> TYPE: PRT
<213> ORGANISM: Artificial Sequence
<220> FEATURE:
<223> OTHER INFORMATION: Alternative LC CDR3 antibody E1

<400> SEQUENCE: 33

Gln Gln Tyr Gly Ser Ser Pro Trp Thr
1               5

<210> SEQ ID NO 34
<211> LENGTH: 5
<212> TYPE: PRT
<213> ORGANISM: Artificial Sequence
<220> FEATURE:
<223> OTHER INFORMATION: HC CDR1 antibody E13

<400> SEQUENCE: 34

Asn Ala Trp Met Ser
1               5

<210> SEQ ID NO 35
<211> LENGTH: 19
<212> TYPE: PRT
<213> ORGANISM: Artificial Sequence
<220> FEATURE:
<223> OTHER INFORMATION: HC CDR2 antibody E13

<400> SEQUENCE: 35

Arg Ile Lys Ser Lys Ile Asp Gly Gly Thr Thr Asp Tyr Ala Ala Pro
1               5                   10                  15

Val Lys Gly

<210> SEQ ID NO 36
<211> LENGTH: 8
<212> TYPE: PRT
<213> ORGANISM: Artificial Sequence
<220> FEATURE:
<223> OTHER INFORMATION: HC CDR3 antibody E13

<400> SEQUENCE: 36

Ala Met Ala Gly Ala Phe Gly Phe
1               5

<210> SEQ ID NO 37
<211> LENGTH: 12
<212> TYPE: PRT
<213> ORGANISM: Artificial Sequence
<220> FEATURE:
<223> OTHER INFORMATION: LC CDR1 antibody E13

<400> SEQUENCE: 37

Arg Ala Ser Gln Ser Val Ser Ser Ser Tyr Leu Ala
1               5                   10

<210> SEQ ID NO 38
<211> LENGTH: 7
<212> TYPE: PRT
<213> ORGANISM: Artificial Sequence
<220> FEATURE:
<223> OTHER INFORMATION: LC CDR2 antibody E13

```
<400> SEQUENCE: 38

Gly Ala Ser Ser Arg Ala Thr
1               5

<210> SEQ ID NO 39
<211> LENGTH: 10
<212> TYPE: PRT
<213> ORGANISM: Artificial Sequence
<220> FEATURE:
<223> OTHER INFORMATION: LC CDR3 antibody E13

<400> SEQUENCE: 39

Gln Gln Tyr Gly Ser Ser Pro Met Tyr Thr
1               5                   10

<210> SEQ ID NO 40
<211> LENGTH: 7
<212> TYPE: PRT
<213> ORGANISM: Artificial Sequence
<220> FEATURE:
<223> OTHER INFORMATION: HC CDR1 antibody E63

<400> SEQUENCE: 40

Ser Gly Gly Tyr Tyr Trp Ser
1               5

<210> SEQ ID NO 41
<211> LENGTH: 16
<212> TYPE: PRT
<213> ORGANISM: Artificial Sequence
<220> FEATURE:
<223> OTHER INFORMATION: HC CDR2 antibody E63

<400> SEQUENCE: 41

Tyr Ile Tyr Tyr Ser Gly Ser Thr Asn Tyr Asn Pro Ser Leu Lys Ser
1               5                   10                  15

<210> SEQ ID NO 42
<211> LENGTH: 12
<212> TYPE: PRT
<213> ORGANISM: Artificial Sequence
<220> FEATURE:
<223> OTHER INFORMATION: HC CDR3 antibody E63

<400> SEQUENCE: 42

Trp Ile Thr Met Phe Arg Gly Val Gly Phe Asp Pro
1               5                   10

<210> SEQ ID NO 43
<211> LENGTH: 11
<212> TYPE: PRT
<213> ORGANISM: Artificial Sequence
<220> FEATURE:
<223> OTHER INFORMATION: LC CDR1 antibody E63

<400> SEQUENCE: 43

Arg Ala Ser Gln Ser Ile Gly Ser Ser Leu His
1               5                   10

<210> SEQ ID NO 44
<211> LENGTH: 7
<212> TYPE: PRT
<213> ORGANISM: Artificial Sequence
<220> FEATURE:
<223> OTHER INFORMATION: LC CDR2 antibody E63
```

```
<400> SEQUENCE: 44

Tyr Ala Ser Gln Ser Phe Ser
1               5

<210> SEQ ID NO 45
<211> LENGTH: 9
<212> TYPE: PRT
<213> ORGANISM: Artificial Sequence
<220> FEATURE:
<223> OTHER INFORMATION: LC CDR3 antibody E63

<400> SEQUENCE: 45

Arg Gln Ser Ser Ser Leu Pro Leu Thr
1               5

<210> SEQ ID NO 46
<211> LENGTH: 5
<212> TYPE: PRT
<213> ORGANISM: Artificial Sequence
<220> FEATURE:
<223> OTHER INFORMATION: HC CDR1 antibody F23

<400> SEQUENCE: 46

Gly Tyr Tyr Trp Asn
1               5

<210> SEQ ID NO 47
<211> LENGTH: 11
<212> TYPE: PRT
<213> ORGANISM: Artificial Sequence
<220> FEATURE:
<223> OTHER INFORMATION: HC CDR2 antibody F23

<400> SEQUENCE: 47

Glu Ile Asn Gln Tyr Asn Pro Ser Leu Lys Ser
1               5                   10

<210> SEQ ID NO 48
<211> LENGTH: 14
<212> TYPE: PRT
<213> ORGANISM: Artificial Sequence
<220> FEATURE:
<223> OTHER INFORMATION: HC CDR3 antibody F23

<400> SEQUENCE: 48

Glu Ile Ala Ile Ala Asp Lys Gly Tyr Tyr Gly Leu Asp Val
1               5                   10

<210> SEQ ID NO 49
<211> LENGTH: 11
<212> TYPE: PRT
<213> ORGANISM: Artificial Sequence
<220> FEATURE:
<223> OTHER INFORMATION: LC CDR1 antibody F23

<400> SEQUENCE: 49

Arg Ala Ser Gln Gly Ile Ser Ser Ala Leu Ala
1               5                   10

<210> SEQ ID NO 50
<211> LENGTH: 7
<212> TYPE: PRT
<213> ORGANISM: Artificial Sequence
<220> FEATURE:
<223> OTHER INFORMATION: LC CDR2 antibody F23

<400> SEQUENCE: 50
```

Asp Ala Ser Ser Leu Glu Ser
1               5

<210> SEQ ID NO 51
<211> LENGTH: 9
<212> TYPE: PRT
<213> ORGANISM: Artificial Sequence
<220> FEATURE:
<223> OTHER INFORMATION: LC CDR3 antibody F23

<400> SEQUENCE: 51

Gln Gln Phe Asn Ser Tyr Pro Leu Thr
1               5

<210> SEQ ID NO 52
<211> LENGTH: 5
<212> TYPE: PRT
<213> ORGANISM: Artificial Sequence
<220> FEATURE:
<223> OTHER INFORMATION: HC CDR1

<400> SEQUENCE: 52

Ser Tyr Tyr Ile His
1               5

<210> SEQ ID NO 53
<211> LENGTH: 14
<212> TYPE: PRT
<213> ORGANISM: Artificial Sequence
<220> FEATURE:
<223> OTHER INFORMATION: HC CDR2

<400> SEQUENCE: 53

Pro Gly Ser Asp Ile Thr Lys Tyr Asn Glu Lys Phe Lys Gly
1               5                   10

<210> SEQ ID NO 54
<211> LENGTH: 10
<212> TYPE: PRT
<213> ORGANISM: Artificial Sequence
<220> FEATURE:
<223> OTHER INFORMATION: HC CDR3

<400> SEQUENCE: 54

Gly Ile Ser Thr Tyr Ser Ala Met Asp Phe
1               5                   10

<210> SEQ ID NO 55
<211> LENGTH: 11
<212> TYPE: PRT
<213> ORGANISM: Artificial Sequence
<220> FEATURE:
<223> OTHER INFORMATION: LC CDR1

<400> SEQUENCE: 55

Lys Ala Ser Gln Asp Val Gly Thr Ala Val Ala
1               5                   10

<210> SEQ ID NO 56
<211> LENGTH: 7
<212> TYPE: PRT
<213> ORGANISM: Artificial Sequence
<220> FEATURE:
<223> OTHER INFORMATION: LC CDR2

<400> SEQUENCE: 56

```
Trp Ala Ser Thr Arg His Thr
1               5

<210> SEQ ID NO 57
<211> LENGTH: 9
<212> TYPE: PRT
<213> ORGANISM: Artificial Sequence
<220> FEATURE:
<223> OTHER INFORMATION: LC CDR3

<400> SEQUENCE: 57

Gln Gln Tyr Ser Ser Tyr Pro Leu Thr
1               5

<210> SEQ ID NO 58
<211> LENGTH: 122
<212> TYPE: PRT
<213> ORGANISM: Artificial Sequence
<220> FEATURE:
<223> OTHER INFORMATION: HC variable region

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Arg Leu Glu Trp Met
            35                  40                  45

Gly Trp Ile Phe Pro Gly Ser Asp Ile Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Gly Ile Ser Thr Tyr Ser Ala Met Asp Phe Trp
            100                 105                 110

Gly Gln Gly Thr Leu Val Thr Val Ser Ser
        115                 120

<210> SEQ ID NO 59
<211> LENGTH: 108
<212> TYPE: PRT
<213> ORGANISM: Artificial Sequence
<220> FEATURE:
<223> OTHER INFORMATION: LC variable region

<400> SEQUENCE: 59

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
                20                  25                  30

Val Ala Trp Tyr Gln Gln Lys Pro Gly Lys Ala Pro Lys Leu Leu Ile
            35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gln Gly Thr Lys Val Glu Ile Lys Arg
```

<210> SEQ ID NO 60
<211> LENGTH: 5
<212> TYPE: PRT
<213> ORGANISM: Artificial Sequence
<220> FEATURE:
<223> OTHER INFORMATION: HC CDR1 of 18E04

<400> SEQUENCE: 60

His Phe Asp Ile Asn
1               5

<210> SEQ ID NO 61
<211> LENGTH: 17
<212> TYPE: PRT
<213> ORGANISM: Artificial Sequence
<220> FEATURE:
<223> OTHER INFORMATION: HC CDR2 of 18E04

<400> SEQUENCE: 61

Trp Met Asn Pro Asp Ser Asp Asn Thr Asp Tyr Ala Gln Glu Phe Gln
1               5                   10                  15
Gly

<210> SEQ ID NO 62
<211> LENGTH: 7
<212> TYPE: PRT
<213> ORGANISM: Artificial Sequence
<220> FEATURE:
<223> OTHER INFORMATION: HC CDR3 of 18E04

<400> SEQUENCE: 62

Gly Gly Thr Thr Leu Asp Tyr
1               5

<210> SEQ ID NO 63
<211> LENGTH: 11
<212> TYPE: PRT
<213> ORGANISM: Artificial Sequence
<220> FEATURE:
<223> OTHER INFORMATION: LC CDR1 of 18E04

<400> SEQUENCE: 63

Ser Gly Asp Ala Leu Pro Lys Lys Tyr Ala Tyr
1               5                   10

<210> SEQ ID NO 64
<211> LENGTH: 7
<212> TYPE: PRT
<213> ORGANISM: Artificial Sequence
<220> FEATURE:
<223> OTHER INFORMATION: LC CDR2 of 18E04

<400> SEQUENCE: 64

Glu Asp Ser Lys Arg Pro Ser
1               5

<210> SEQ ID NO 65
<211> LENGTH: 11
<212> TYPE: PRT
<213> ORGANISM: Artificial Sequence
<220> FEATURE:
<223> OTHER INFORMATION: LC CDR3 of 18E04

<400> SEQUENCE: 65

Tyr Ser Thr Asp Ser Ser Asp Asn His Val Ile
1               5                   10

<210> SEQ ID NO 66
<211> LENGTH: 5
<212> TYPE: PRT
<213> ORGANISM: Artificial Sequence
<220> FEATURE:
<223> OTHER INFORMATION: HC CDR1 of 98C07

<400> SEQUENCE: 66

Asp Tyr Tyr Met Ser
1               5

<210> SEQ ID NO 67
<211> LENGTH: 16
<212> TYPE: PRT
<213> ORGANISM: Artificial Sequence
<220> FEATURE:
<223> OTHER INFORMATION: HC CDR2 of 98C07

<400> SEQUENCE: 67

Tyr Ile Ser Arg Ser Ser Phe Ile Tyr Tyr Ser Glu Ser Val Lys Gly
1               5                   10                  15

<210> SEQ ID NO 68
<211> LENGTH: 8
<212> TYPE: PRT
<213> ORGANISM: Artificial Sequence
<220> FEATURE:
<223> OTHER INFORMATION: HC CDR3 of 98C07

<400> SEQUENCE: 68

Trp Glu Leu Ser Pro Phe Asp Tyr
1               5

<210> SEQ ID NO 69
<211> LENGTH: 11
<212> TYPE: PRT
<213> ORGANISM: Artificial Sequence
<220> FEATURE:
<223> OTHER INFORMATION: LC CDR1 of 98C07

<400> SEQUENCE: 69

Arg Ala Ser Gln Gly Ile Ser Asn Tyr Leu Ala
1               5                   10

<210> SEQ ID NO 70
<211> LENGTH: 7
<212> TYPE: PRT
<213> ORGANISM: Artificial Sequence
<220> FEATURE:
<223> OTHER INFORMATION: LC CDR2 of 98C07

<400> SEQUENCE: 70

Ala Ala Ser Ser Leu Gln Ser
1               5

<210> SEQ ID NO 71
<211> LENGTH: 9
<212> TYPE: PRT
<213> ORGANISM: Artificial Sequence
<220> FEATURE:
<223> OTHER INFORMATION: LC CDR3 of 98C07

<400> SEQUENCE: 71

Gln Gln Tyr Asn Thr Tyr Pro Phe Thr

<210> SEQ ID NO 72
<211> LENGTH: 5
<212> TYPE: PRT
<213> ORGANISM: Artificial Sequence
<220> FEATURE:
<223> OTHER INFORMATION: HC CDR1 of 1C02

<400> SEQUENCE: 72

Tyr Tyr Gly Ile Ser
1               5

<210> SEQ ID NO 73
<211> LENGTH: 17
<212> TYPE: PRT
<213> ORGANISM: Artificial Sequence
<220> FEATURE:
<223> OTHER INFORMATION: HC CDR2 of 1C02

<400> SEQUENCE: 73

Trp Ile Ser Ala Asn Ser Gly Asn Thr Asn Tyr Ala Gln Lys Phe Gln
1               5                   10                  15

Gly

<210> SEQ ID NO 74
<211> LENGTH: 8
<212> TYPE: PRT
<213> ORGANISM: Artificial Sequence
<220> FEATURE:
<223> OTHER INFORMATION: HC CDR3 of 1C02

<400> SEQUENCE: 74

Gly Gly Val Ala Val Leu Glu Tyr
1               5

<210> SEQ ID NO 75
<211> LENGTH: 11
<212> TYPE: PRT
<213> ORGANISM: Artificial Sequence
<220> FEATURE:
<223> OTHER INFORMATION: LC CDR1 of 1C02

<400> SEQUENCE: 75

Trp Ala Ser Gln Gly Ile Ser Ser Tyr Leu Ala
1               5                   10

<210> SEQ ID NO 76
<211> LENGTH: 7
<212> TYPE: PRT
<213> ORGANISM: Artificial Sequence
<220> FEATURE:
<223> OTHER INFORMATION: LC CDR2 of 1C02

<400> SEQUENCE: 76

Val Ala Ser Thr Leu Gln Ser
1               5

<210> SEQ ID NO 77
<211> LENGTH: 9
<212> TYPE: PRT
<213> ORGANISM: Artificial Sequence
<220> FEATURE:
<223> OTHER INFORMATION: LC CDR3 of 1C02

<400> SEQUENCE: 77

Gln Gln Leu Lys Ile Tyr Pro Leu Thr
1               5

<210> SEQ ID NO 78
<211> LENGTH: 5
<212> TYPE: PRT
<213> ORGANISM: Artificial Sequence
<220> FEATURE:
<223> OTHER INFORMATION: HC CDR1 of 1C06

<400> SEQUENCE: 78

Asp Tyr Tyr Met Asn
1               5

<210> SEQ ID NO 79
<211> LENGTH: 17
<212> TYPE: PRT
<213> ORGANISM: Artificial Sequence
<220> FEATURE:
<223> OTHER INFORMATION: HC CDR2 of 1C06

<400> SEQUENCE: 79

Asp Ile Ser Ser Arg Asp Asn Thr Ile Tyr Tyr Ala Asp Ser Val Lys
1               5                   10                  15

Gly

<210> SEQ ID NO 80
<211> LENGTH: 14
<212> TYPE: PRT
<213> ORGANISM: Artificial Sequence
<220> FEATURE:
<223> OTHER INFORMATION: HC CDR3 of 1C06

<400> SEQUENCE: 80

Ala Arg Glu Arg Gly Phe Gly Asp Tyr Phe Gly Met Asp Val
1               5                   10

<210> SEQ ID NO 81
<211> LENGTH: 11
<212> TYPE: PRT
<213> ORGANISM: Artificial Sequence
<220> FEATURE:
<223> OTHER INFORMATION: LC CDR1 of 1C06

<400> SEQUENCE: 81

Arg Ala Ser Gln Asp Ile Ser Ser Ala Leu Ala
1               5                   10

<210> SEQ ID NO 82
<211> LENGTH: 7
<212> TYPE: PRT
<213> ORGANISM: Artificial Sequence
<220> FEATURE:
<223> OTHER INFORMATION: LC CDR2 of 1C06

<400> SEQUENCE: 82

Asp Ala Ser Ser Leu Glu Ser
1               5

<210> SEQ ID NO 83
<211> LENGTH: 9
<212> TYPE: PRT
<213> ORGANISM: Artificial Sequence
<220> FEATURE:
<223> OTHER INFORMATION: LC CDR3 of 1C06

<400> SEQUENCE: 83

```
Gln Gln Phe Asn Thr Tyr Pro Leu Thr
1               5

<210> SEQ ID NO 84
<211> LENGTH: 21
<212> TYPE: DNA
<213> ORGANISM: Artificial Sequence
<220> FEATURE:
<223> OTHER INFORMATION: DcR3 siRNA sense strand

<400> SEQUENCE: 84
gccaggcucu uccucccaut t                                          21

<210> SEQ ID NO 85
<211> LENGTH: 21
<212> TYPE: DNA
<213> ORGANISM: Artificial Sequence
<220> FEATURE:
<223> OTHER INFORMATION: DcR3 siRNA antisense strand

<400> SEQUENCE: 85
augggaggaa gagccuggct t                                          21

<210> SEQ ID NO 86
<211> LENGTH: 21
<212> TYPE: DNA
<213> ORGANISM: Artificial Sequence
<220> FEATURE:
<223> OTHER INFORMATION: control siRNA sense strand

<400> SEQUENCE: 86
gcccgcuuuc ccucagcaut t                                          21

<210> SEQ ID NO 87
<211> LENGTH: 19
<212> TYPE: DNA
<213> ORGANISM: Artificial Sequence
<220> FEATURE:
<223> OTHER INFORMATION: control siRNA antisense strand

<400> SEQUENCE: 87
augcugaggg aaagcgggc                                             19
```

METHODS OF TREATING AUTOIMMUNE CONDITIONS IN PATIENTS WITH GENETIC VARIATIONS IN DCR3 OR IN A DCR3 NETWORK GENE

CROSS-REFERENCE TO RELATED APPLICATIONS

This application claims priority to U.S. Provisional Application Nos. 62/208,383, filed Aug. 21, 2015, and 62/320,400, filed Apr. 8, 2016, both of which are incorporated by reference herein in their entirety.

FIELD OF THE INVENTION

The present disclosure relates to methods of treating autoimmune conditions in patients who have a genetic alteration in the TNFRSF6B gene, which codes for the decoy receptor 3 protein (DcR3), for example that reduce the expression, secretion, or ligand binding activity of DcR3, or who have a genetic alteration in a gene of the TNFRSF6B/DcR3 signaling network. For example, in some embodiments, the conditions may be treated with molecules that inhibit the activity of DcR3 ligands such as LIGHT, TL1A, and FasL, such as anti-LIGHT, anti-TL1A, and anti-FasL antibodies, or inhibitors of the non-canonical NF-κB pathway.

BACKGROUND OF THE INVENTION

Several publications and patent documents are cited throughout the specification in order to describe the state of the art to which this invention pertains. Each of these citations is incorporated by reference herein as though set forth in full.

A genome-wide association study (GWAS) previously carried out in a cohort of 1,011 individuals with pediatric-onset inflammatory bowel disease (IBD) and 4,250 matched controls, identified and replicated a significantly associated, previously unreported locus on chromosome 20q13 carrying allelic variants. The locus is close to the TNFRSF6B gene, which encodes the Decoy Receptor 3 (DcR3) protein. Subsequently, sequencing of the TNFRSF6B gene in 528 pediatric IBD sufferers and 549 healthy control individuals uncovered several missense variants at the TNFRSF6B locus that are enriched in the IBD sufferers compared to controls, some of which may affect DcR3 secretion in cultured cells. (Cardinale et al., *Genes and Immunity* 14: 447-452 (2013).)

The present application further includes data showing that allelic variation in the TNFRSF6B locus is correlated with other autoimmune conditions including psoriasis and thyroiditis.

DcR3 binds to cytokines of the tumor necrosis factor (TNF) superfamily, namely TL1A (TNFSF15), LIGHT (TNFSF14) and Fas ligand (FASLG), and blocks their ability to stimulate their receptors. TL1A, for example, is also a ligand for the death-domain receptor 3 (DR3) protein. Binding of TL1A to DR3 may induce secretion of IFN-gamma by T cells and may activate the NF-κB pathway. DcR3 may compete with DR3 for TL1A binding, thus controlling its stimulatory effects on T cells. Genetic alterations in the DcR3 gene TNFRSF6B, for example those causing a reduction in DcR3 secretion or in ligand binding, as well as mutations affecting DcR3 expression levels, may cause unopposed inflammatory signals as DcR3 may be less effective in downregulating its ligands such as TL1A or LIGHT. Similarly, the inventors herein have recognized that genetic alterations in other genes in this pathway, such as the genes for DR3 (TNFRSF25), TL1A (TNFSF15), LIGHT (TNFSF14), FasL (FASLG), as well as Fas receptor (FASR; CD95), Herpes virus entry mediator A (HVEM or TNFRSF14), and lymphotoxins A and B (LTA and LTB) and their receptors, may similarly compromise the normal functioning of the DR3/DcR3 regulatory system.

Accordingly, the inventors have recognized that inhibitors of DcR3 ligands such as TL1A, LIGHT, and Fas ligand (FasL), for example anti-TL1A, anti-LIGHT, or anti-FasL antibodies or small molecule inhibitors, may be particularly useful in IBD subjects who have a DcR3 genetic alteration (i.e. that harbor a TNFRSF6B allelic variant) or who have a genetic alteration in another gene in this pathway. Data herein also show that DR3/DcR3 also may regulate the non-canonical NF-κB pathway. Thus, inhibitors of the non-canonical NF-κB pathway are further drug targets for autoimmune disease patients harboring genetic alterations in TNFRSF6B or in a TNFRSF6B/DcR3 pathway gene.

SUMMARY OF THE INVENTION

The present disclosure includes, for example, a method of treating an autoimmune disease (AID) in an adult or pediatric patient in need thereof, comprising:
(a) determining whether the patient harbors at least one genetic alteration in at least one DcR3 network gene, such as at least one genetic alteration in TNFRSF6B associated with reduced DcR3 level or activity, such as associated with reduced expression or secretion of DcR3 or reduction in DcR3 ligand binding activity; and, if the patient harbors such a mutation,
(b) administering to the patient an effective amount of a DcR3 ligand inhibitor.

The present disclosure also includes methods of treating an autoimmune disease in an adult or pediatric patient in need thereof, wherein the patient harbors at least one genetic alteration in at least one DcR3 network gene, such as at least one genetic alteration in TNFRSF6B associated with reduced DcR3 level or activity, such as associated with reduced expression or secretion of DcR3 or reduction in DcR3 ligand binding activity, comprising administering an effective amount of a DcR3 ligand inhibitor to the patient. In some of the above embodiments, the DcR3 network gene is one or more of DcR3, DR3, TL1A, LIGHT, FasL, HVEM, LTA, LTB, FasR (CD95), and LIGHT receptor. In some embodiments, the DcR3 network gene is one or more of TNFRSF6B, CSF2, TNF, INS-IGF2, ERBB3, TNFSF15, HSPA1A, HSPA1B, DAXX, TRAIP, CUL2, GPX1, NOD2, INS, RHOA, INPP5D, DDAH2, LTB, RTEL1, LTA, IL4, CLN3, CARD9, SMAD3, IGF2, NFKBIL1, BCL2L11, PPIF, CDKN1A, NOTCH1, PLA2G4A, NUPR1, JAK2, IL12B, LRRK2, IL2, DAP3.

In some embodiments, at least one genetic alteration in at least one DcR3 network gene is associated with increased T cell activity and/or increased production of IFN-gamma.

In some embodiments, the autoimmune disease to be treated is one or more of ankylosing spondylitis (AS), psoriasis (PS or PSOR), celiac disease (CEL), systemic lupus erythematosus (SLE), common variable immunodeficiency (CVID), inflammatory bowel disease (IBD) ulcerative colitis (UC), type I diabetes (T1D), juvenile idiopathic arthritis (JIA), Crohn's disease (CD), alopecia areata (AA), multiple sclerosis (MS), primary biliary cirrhosis (PBC), primary sclerosing cholangitis (PSC), rheumatoid arthritis (RA), Sjogren's syndrome (SJO), systemic sclerosis (SSC), spondyoarthropathy (SPA), vitiligo (VIT), asthma, or thyroiditis (AITD, THY or TH). In some embodiments the subject to be treated is hypo-responsive to TNF alpha monoclonal antibody therapy. In some embodiments, the subject has developed or is developing resistance to TNF alpha monoclonal antibody therapy. In any such embodiments, determining whether the patient harbors at least one genetic alteration may comprise amplification and sequencing of the DcR3 network gene or a transcript of the gene, or hybridization of one or more nucleic acid probes to the gene.

In some embodiments, the DcR3 network genetic alteration comprises one or more of those shown in the tables of Example III below. The genetic alteration in TNFRSF6B may be, but is not limited to, one or more of Gly6Arg, Pro23Leu, Gly29Arg, Ala102Thr, Arg103Gln, Arg116His, Gly124Val, Arg172His, Gly178Asp, Gly178Glu, Cys211Gly, Val215Ile, Ala220Val, Arg258Cys, Arg281Cys, and Val282Met, based on the wild-type DcR3 sequence provided in SEQ ID NO:1 herein. In some cases, the genetic alteration is one that is associated with a secretion defective DcR3 phenotype, such as Gly29Arg, Arg116His, Arg172His, Gly178Glu or Asp, Cys211Gly, or Arg258Cys, or one that is associated with reduced DcR3 expression, or that is associated with reduced DcR3 ligand binding activity.

The DcR3 ligand inhibitor may be an inhibitor of LIGHT, TL1A, or FasL, for example. The DcR3 ligand inhibitor may be an antibody, ligand trap, nucleic acid such as an antisense nucleic acid or siRNA, or an aptamer of DcR3. The inhibitor may be an anti-LIGHT antibody, anti-TL1A antibody, or anti-FasL antibody. Where the DcR3 ligand inhibitor is an anti-LIGHT antibody, it may comprise a heavy chain and a light chain that together comprise one of the following sets of CDR-H1, CDR-H2, CDR-H3, CDR-L1, CDR-L2, and CDR-L3 amino acid sequences:

SEQ ID NOs: 2, 3, 4, 5, 6, and 7;
SEQ ID NOs: 10, 11, 12, 13, 14, and 15;
SEQ ID NOs: 16, 17, 18, 19, 20, and 21;
SEQ ID NOs: 22, 23, 24, 25, 26, and 27;
SEQ ID NOs: 28, 29, 30, 31, 32, and 33;
SEQ ID NOs: 34, 35, 36, 37, 38, and 39;
SEQ ID NOs: 40, 41, 42, 43, 44, and 45;
SEQ ID NOs: 46, 47, 48, 49, 50, and 51; and
SEQ ID NOs: 52, 53, 54, 55, 56, and 57.

In some embodiments, the anti-LIGHT antibody may comprise heavy and light chain variable regions with at least 85%, such as at least 90%, at least 95%, at least 98%, or at least 99% identity to SEQ ID NOs: 8 and 9 or SEQ ID NOs: 58 and 59. In other embodiments, the anti-LIGHT antibody may comprise the CDR-H1, CDR-H2, CDR-H3, CDR-L1, CDR-L2, and CDR-L3 amino acid sequences of any one of antibodies 1C02, 13H04, 31A10, 1C06, 98C07, 18E04, 42A02, 29C09, 14B09, 117C06, 114F05, or 62C01 described in WO 2015/107331. For example, it may comprise one of the following sets of CDR-H1, CDR-H2, CDR-H3, CDR-L1, CDR-L2, and CDR-L3 amino acid sequences: SEQ ID NOs: 60, 61, 62, 63, 64, and 65; SEQ ID NOs: 66, 67, 68, 69, 70, and 71; SEQ ID NOs: 72, 73, 74, 75, 76, and 77; or SEQ ID NOs: 78, 79, 80, 81, 82, and 83. Additional anti-LIGHT antibodies are described in the detailed description section below.

In some of the therapeutic treatment embodiments described above, the DcR3 ligand inhibitor is not a TL1A inhibitor. In some embodiments, it is not an anti-TL1A antibody. In some embodiments, it is not a FasL inhibitor. In some embodiments, it is not an anti-FasL antibody.

The present disclosure further includes methods of treating an autoimmune disease in an adult or pediatric patient in need thereof, wherein the patient harbors at least one genetic alteration in at least on DcR3 network gene, such as at least one genetic alteration in TNFRSF6B associated with reduced DcR3 level or activity, such as associated with reduced expression or secretion of DcR3 or reduction in DcR3 ligand binding activity, comprising administering an effective amount of a non-canonical NF-κB inhibitor to the patient. In some of the above embodiments, the DcR3 network gene is one or more of DcR3, DR3, TL1A, LIGHT, FasL, HVEM, LTA, LTB, FasR(CD95), and LIGHT receptor. In some embodiments, the DcR3 network gene is one or more of TNFRSF6B, CSF2, TNF, INS-IGF2, ERBB3, TNFSF15, HSPA1A, HSPA1B, DAXX, TRAIP, CUL2, GPX1, NOD2, INS, RHOA, INPP5D, DDAH2, LTB, RTEL1, LTA, IL4, CLN3, CARD9, SMAD3, IGF2, NFK-BIL1, BCL2L11, PPIF, CDKN1A, NOTCH1, PLA2G4A, NUPR1, JAK2, IL12B, LRRK2, IL2, DAP3. In some embodiments, the at least one genetic alteration in the at least one DcR3 network gene is associated with increased T cell activity and/or increased production of IFN-gamma.

In some embodiments, the autoimmune disease to be treated is one or more of ankylosing spondylitis (AS), psoriasis (PS or PSOR), celiac disease (CEL), systemic lupus erythematosus (SLE), common variable immunodeficiency (CVID), inflammatory bowel disease (IBD) ulcerative colitis (UC), type I diabetes (T1D), juvenile idiopathic arthritis (JIA), Crohn's disease (CD), alopecia areata (AA), multiple sclerosis (MS), primary biliary cirrhosis (PBC), primary sclerosing cholangitis (PSC), rheumatoid arthritis (RA), Sjogren's syndrome (SJO), systemic sclerosis (SSC), spondyoarthropathy (SPA), vitiligo (VIT), asthma, or thyroiditis (AITD, THY or TH). In some embodiments the subject to be treated is hypo-responsive to TNF alpha monoclonal antibody therapy. In some embodiments, the subject has developed or is developing resistance to TNF alpha monoclonal antibody therapy. In any such embodiments, determining whether the patient harbors at least one genetic alteration may comprise amplification and sequencing of the gene or a transcript of the gene, or hybridization of one or more nucleic acid probes to the gene.

In some embodiments, the DcR3 network genetic alteration comprises one or more of those shown in the tables of Example III below. The genetic alteration in TNFRSF6B may be, but is not limited to, one or more of Gly6Arg, Pro23Leu, Gly29Arg, Ala102Thr, Arg103Gln, Arg116His, Gly124Val, Arg172His, Gly178Asp, Gly178Glu, Cys211Gly, Val215Ile, Ala220Val, Arg258Cys, Arg281Cys, and Val282Met, based on the wild-type DcR3 sequence provided in SEQ ID NO:1 herein. In some cases, the genetic alteration is one that is associated with a secretion defective DcR3 phenotype, such as Gly29Arg, Arg116His, Arg172His, Gly178Glu or Asp, Cys211Gly, or Arg258Cys, or one that is associated with reduced DcR3 expression, or that is associated with reduced DcR3 ligand binding activity.

In some of the therapeutic treatment embodiments described above, the DcR3 ligand inhibitor is not a TL1A inhibitor. In some embodiments, it is not an anti-TL1A antibody. In some embodiments, it is not a FasL inhibitor. In some embodiments, it is not an anti-FasL antibody.

The present disclosure also includes methods for identifying a therapeutic agent, comprising
(a) providing cells expressing at least one genetic alteration in TNFRSF6B associated with reduced DcR3 level or activity, such as associated with reduced expression or secretion of DcR3 or reduction in DcR3 ligand binding activity;

(b) providing cells that comprise a wild-type TNFRSF6B allele;

(c) contacting the cells of a) and b) with a test agent; and (d) determining whether the agent alters immune signaling of the cells of a) relative to those of b).

In some embodiments, the agent alters at least one parameter selected from IκB homeostasis, FasL induced apoptosis, DcR3-LIGHT association, LIGHT, HVEM, LTBR, TL1A, or DC160 function, and non-canonical NF-κB signaling.

BRIEF DESCRIPTION OF THE DRAWINGS

(FIG. 5A) Lysates from $10^6$ cells of non-secretors, control and patient cells with three different combinations of risk variants (1/1, 1/2 and 2/2) were separated by SDS-PAGE and evaluated for Caspase-8, Caspase-3, Caspase-9 and Bcl-2 in TNF-α activated time course experiment. Blots were stripped and reprobed for β-actin as a loading control. Numbers beneath each lane represent densitometric ratios of candidate protein normalized to the 0 minute time point and loading control. (FIG. 5B) Bar graph for expression levels and fold change over time of caspase-8, caspase-3, caspase-9 and Bcl-2.

(FIG. 6A) Cytoplasmic and nuclear levels of specific NF-κB members was monitored by immunoblot analysis. Blots were stripped and reprobed for -actin as a loading control in cytolpsmic extracts. No β-actin in nuclear extracts represents the purity of nuclear extracts. Numbers beneath each lane represent densitometric ratios of candidate protein normalized to the 0 minute time point and loading control. (FIG. 6B) Bar graph represents fold change in cytoplasmic and nuclear expression levels of specific NF-κB members in non-secretor (●), control (■) and patient cells (▲) with three different combinations of risk variants (1/1, 1/2 and 2/2) monitored by immunoblot analysis in a time course experiment.

(FIG. 7A) & (FIG. 7B) shows the decrease in DcR3 expression post nuclecofection of P (1/2) EBV cells with control siRNA and DcR3 siRNA. (FIG. 7C) Represents effect of DcR3 knockdown on cell proliferation measured by MTT assay in patient cells with three different combinations of risk variants (1/1, 1/2 and 2/2).

DETAILED DESCRIPTION OF THE INVENTION

Figure 1:
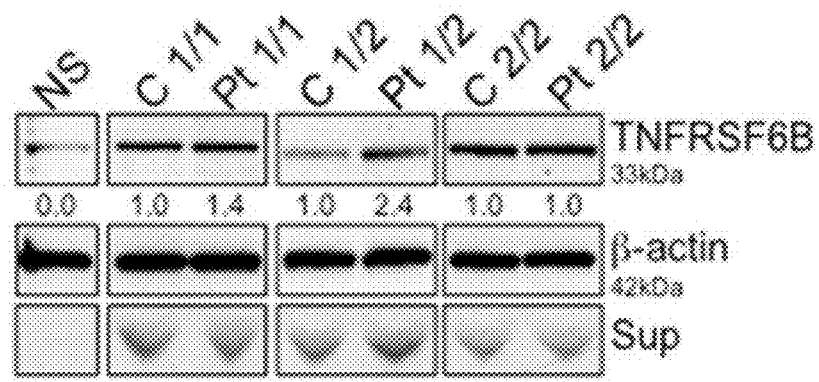
FIG. 1. DcR3 western blot analysis. The whole cell lysate of non-secretor, control and patient derived EBV cells was analyzed for DcR3 expression. 1 stands for A or T. 2 stands for G or C. Blots were stripped and reprobed for β-actin as a loading control; numbers beneath each lane represent densitometric ratios of candidate protein normalized to the loading control.

The following definitions are provided to facilitate an understanding of the invention. They are not intended to limit the invention in any way.

Definitions

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an "isolated," or "biologically pure" molecule is a compound that has been removed from its natural milieu. As such, the terms "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

An "AutoImmune Disease (AID)" or "autoimmune condition" as used herein, includes but is not limited to, one or more of ankylosing spondylitis (AS), psoriasis (PS or PSOR), celiac disease (CEL), systemic lupus erythematosus (SLE), common variable immunodeficiency (CVID), inflammatory bowel disease (IBD) ulcerative colitis (UC), type I diabetes (T1D), juvenile idiopathic arthritis (JIA), Crohn's disease (CD), alopecia areata (AA), multiple sclerosis (MS), primary biliary cirrhosis (PBC), primary sclerosing cholangitis (PSC), rheumatoid arthritis (RA), Sjogren's syndrome (SJO), systemic sclerosis (SSC), spondyoarthropathy (SPA), vitiligo (VIT), asthma, or thyroiditis (AITD, THY or TH). In some embodiments the subject to be treated is hypo-responsive to TNF alpha monoclonal antibody therapy. In some embodiments, the subject has developed or is developing resistance to TNF alpha monoclonal antibody therapy. Autoimmune diseases herein may include diseases affecting adults as well as pediatric subjects, i.e. pediatric autoimmune diseases (pAIDs). AIDs include pAIDs herein.

A "pediatric" subject herein is a human of less than 18 years of age, whereas an "adult" subject is 18 years or older.

"Decoy Receptor 3 (DcR3)" is a secreted soluble decoy receptor protein that binds, for example, to TL1A, LIGHT, and FasL proteins and that may inhibit their activities. DcR3 may also act to directly or indirectly inhibit the interactions of LIGHT with HVEM and lymphotoxin beta receptor (LTβR) and FasL with Fas. DcR3 is a TNF receptor super family member and is encoded by the TNFRSF6B gene.

The terms "TNFRSF6B network" or "DcR3 network" herein refer interchangeably to a group of proteins (or the genes that encode them depending on context) that are within two degrees of DcR3. In other words, the "network" comprises (a) DcR itself, (b) proteins to which DcR3 binds or that directly regulate (e.g. activate or deactivate) or are directly regulated by DcR3, such as TL1A, LIGHT, and FasL, and (c) proteins that directly regulate or are directly regulated by the proteins of (b), such as DR3 and HVEM (LIGHT receptor). The "network" herein includes, for example, DcR3, DR3, lymphotoxins A and B (LTA and LTB), FasL, TL1A, LIGHT, HVEM, and Fas receptor (FasR or CD95). The DcR3 network genes may also include TNFRSF6B, CSF2, TNF, INS-IGF2, ERBB3, TNFSF15, HSPA1A, HSPA1B, DAXX, TRAIP, CUL2, GPX1, NOD2, INS, RHOA, INPP5D, DDAH2, LTB, RTEL1, LTA, IL4, CLN3, CARD9, SMAD3, IGF2, NFKBIL1, BCL2L11, PPIF, CDKN1A, NOTCH1, PLA2G4A, NUPR1, JAK2, IL12B, LRRK2, IL2, and DAP3, mutations in which genes have been found to be enriched in pAID sufferers compared to controls along with mutations in DcR3.

"DcR3 variants" herein include DcR3 proteins with modifications such that they differ from the human DcR3 sequence provided in SEQ ID NO: 1. They may be encoded by a TNFRSF6B gene sequence having at least one genetic alteration, i.e. a "TNFRSF6B variant" allele. Apoptosis signaling may also be altered in cells expressing DcR3 variants. DcR3 variants may also exhibit altered capacity to interact with at least one DcR3 ligand or DcR3 ligand interacting protein, such as FasL, LIGHT, HVEM, LTBR, TL1A, and CD160. The properties of DcR3 variants may give rise to an altered risk for the development of one or more AIDs compared to risk in subjects lacking such variants. "Secretion defective variants of decoy receptor 3 (DcR3)" or "secretion defective DcR3 variants" are DcR3 proteins that show reduced DcR3 secretion levels compared to wild-type DcR3.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence, and copy-number variations. The term "genetic alteration" may also be applied to a protein and encompasses without limitation amino acid substitutions, insertions, and deletions. An "allelic variation" refers to the presence of an allele that differs from a wild-type or reference allele, i.e. one allele that has a genetic alteration in comparison to a wild-type or reference allele. For example, a person may have an allelic variation at TNFRSF6B if they are heterozygous or homozygous for an allele different from the designated wild-type TNFRSF6B allele. In some embodiments, an allelic variant TNFRSF6B gives rise to a genetic alteration in the DcR3 protein.

In some embodiments, the allelic variant in TNFRSF6B may be associated with a reduction in DcR3 activity. For example, in some cases, a genetic alteration in TNFRSF6B or in DcR3 leads to an observed reduction in DcR3 level or activity, such as due to a decrease in expression of DcR3, a reduction in the cellular secretion of DcR3 (a "secretion defective" alteration) for instance as evidence by a reduced level of DcR3 in cell supernatants compared to a wild-type control, and/or a reduction in ligand binding by DcR3 to one or more of its ligands such as TL1A, LIGHT, and FasL.

A "single nucleotide variation (SNV)," also interchangeably referred to as a "single nucleotide polymorphism (SNP)" herein, refers to a change in which a single base in the DNA differs from the usual base at that position. These single base changes are often called SNPs or "snips." Millions of SNP's have been cataloged in the human genome. Some SNPs such as that which causes sickle cell are responsible for disease. Other SNPs are normal variations in the genome.

"AID-associated SNP or AID-associated specific marker" or "AID-associated marker" is an SNP or marker that is associated with an increased risk of developing an AID and that is found at a lower frequency or is not generally found in normal subjects who do not have the AID. Such markers may include but are not limited to nucleic acids, proteins encoded thereby, or other small molecules. In some cases, the SNP or marker is an AID-associated SNP or AID-associated marker.

The term "DcR3 ligand inhibitor" refers to a molecule that inhibits the function of a DcR3 ligand such as FasL, LIGHT, or TL1A. DcR3 ligand inhibitors may include small molecules or biologics, and may include antagonist antibodies that bind to a DcR3 ligand such as FasL, LIGHT, or TL1A as well as proteins that act as traps for those ligands.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. As used herein, the term refers to a molecule comprising at least complementarity-determining region (CDR) 1, CDR2, and CDR3 of a heavy chain and at least CDR1, CDR2, and CDR3 of a light chain, wherein the molecule is capable of binding to antigen. The term antibody includes, but is not limited to, fragments that are capable of binding antigen, such as Fv, single-chain Fv (scFv), Fab, Fab', and (Fab')$_2$. The term antibody also includes, but is not limited to, chimeric antibodies, humanized antibodies, human antibodies, and antibodies of various species such as mouse, cynomolgus monkey, etc.

The term "heavy chain" refers to a polypeptide comprising at least a heavy chain variable region, with or without a leader sequence. In some embodiments, a heavy chain comprises at least a portion of a heavy chain constant region. The term "full-length heavy chain" refers to a polypeptide comprising a heavy chain variable region and a heavy chain constant region, with or without a leader sequence.

The term "heavy chain variable region" refers to a region comprising a heavy chain complementary determining region (CDR) 1, framework region (FR) 2, CDR2, FR3, and CDR3 of the heavy chain. In some embodiments, a heavy chain variable region also comprises at least a portion of an FR1 and/or at least a portion of an FR4. In some embodiments, a heavy chain CDR1 corresponds to Kabat residues 31 to 35; a heavy chain CDR2 corresponds to Kabat residues 50 to 65; and a heavy chain CDR3 corresponds to Kabat residues 95 to 102. See, e.g., Kabat Sequences of Proteins of Immunological Interest (1987 and 1991, NIH, Bethesda, Md.).

The term "light chain" refers to a polypeptide comprising at least a light chain variable region, with or without a leader sequence. In some embodiments, a light chain comprises at least a portion of a light chain constant region. The term "full-length light chain" refers to a polypeptide comprising a light chain variable region and a light chain constant region, with or without a leader sequence. The term "light chain variable region" refers to a region comprising a light chain CDR1, FR2, HVR2, FR3, and HVR3. In some embodiments, a light chain variable region also comprises an FR1 and/or an FR4. In some embodiments, a light chain CDR1 corresponds to Kabat residues 24 to 34; a light chain CDR2 corresponds to Kabat residues 50 to 56; and a light chain CDR3 corresponds to Kabat residues 89 to 97. See, e.g., Kabat Sequences of Proteins of Immunological Interest (1987 and 1991, NIH, Bethesda, Md.).

A "chimeric antibody" refers to an antibody in which a portion of the heavy and/or light chain is derived from a particular source or species, while the remainder of the heavy and/or light chain is derived from a different source or species. In some embodiments, a chimeric antibody refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, all of the variable regions of a chimeric antibody are from a first species and all of the constant regions of the chimeric antibody are from a second species.

A "humanized antibody" refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is an Fab, an scFv, a (Fab')$_2$, etc.

A "human antibody" as used herein refers to antibodies produced in humans, antibodies produced in non-human animals that comprise human immunoglobulin genes, such as XenoMouse®, and antibodies selected using in vitro methods, such as phage display, wherein the antibody repertoire is based on a human immunoglobulin sequences.

The term "leader sequence" refers to a sequence of amino acid residues located at the N terminus of a polypeptide that facilitates secretion of a polypeptide from a mammalian cell. A leader sequence may be cleaved upon export of the polypeptide from the mammalian cell, forming a mature protein. Leader sequences may be natural or synthetic, and they may be heterologous or homologous to the protein to which they are attached.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

The terms "inhibition" or "inhibit" refer to a decrease or cessation of any event (such as protein ligand binding) or to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. It is not necessary that the inhibition or reduction be complete. For example, in certain embodiments, by "reduce" or "inhibit" is meant the ability to cause an overall decrease of 20% or greater. In another embodiment, by "reduce" or "inhibit" is meant the ability to cause an overall decrease of 50% or greater. In yet another embodiment, by "reduce" or "inhibit" is meant the ability to cause an overall decrease of 75%, 85%, 90%, 95%, or greater.

"Linkage" describes the tendency of genes, alleles, loci or genetic markers to be inherited together as a result of their location on the same chromosome, and is measured by percent recombination (also called recombination fraction, or θ) between the two genes, alleles, loci or genetic markers. The closer two loci physically are on the chromosome, the lower the recombination fraction will be. Normally, when a polymorphic site from within a disease-causing gene is tested for linkage with the disease, the recombination fraction will be zero, indicating that the disease and the disease-causing gene are always co-inherited. In rare cases, when a gene spans a very large segment of the genome, it may be possible to observe recombination between polymorphic sites on one end of the gene and causative mutations on the other. However, if the causative mutation is the polymorphism being tested for linkage with the disease, no recombination will be observed.

"Centimorgan" is a unit of genetic distance signifying linkage between two genetic markers, alleles, genes or loci, corresponding to a probability of recombination between the two markers or loci of 1% for any meiotic event.

"Linkage disequilibrium" or "allelic association" means the preferential association of a particular allele, locus, gene or genetic marker with a specific allele, locus, gene or genetic marker at a nearby chromosomal location more frequently than expected by chance for any particular allele frequency in the population.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose.

The phrase "consisting essentially of" when referring to a particular nucleotide or amino acid means a sequence having the properties of a given SEQ ID NO: or compound. For example, when used in reference to an amino acid sequence, the phrase includes the sequence per se and molecular modifications that would not affect the functional and novel characteristics of the sequence. Similarly, the phrase refers to compounds with modifications that do not affect the functional and novel characteristics of the parent compound. Methods can also consist essentially of a recited series of steps.

"Target nucleic acid" as used herein refers to a previously defined region of a nucleic acid present in a complex nucleic acid mixture wherein the defined wild-type region contains at least one known nucleotide variation that may or may not be associated with AID. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process includes the construction of a cDNA library from mRNA and isolation of distinct cDNA clones and yields an approximately $10^6$ fold purification of the native message. Thus, purification of at least one order of magnitude, preferably two or three orders, and more preferably four or five orders of magnitude is expressly contemplated. Thus the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule. Levels of complementarity between selectively hybridizing nucleic acids can vary but is typically greater than 80% and is preferably between 90-95%.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary") with enough sequence specificity to distinguish the target sequence over non-target sequences. In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence that hybridizes to any AID specific marker nucleic acid, but does not hybridize to other nucleotides. Also polynucleotide that "specifically hybridizes" may hybridize only to a single AID-specific marker shown in the Tables contained herein. Appropriate conditions enabling specific hybridization of single stranded nucleic acid molecules of varying complementarity are well known to those of skill in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989):

$$T_m = 81.5"C + 16.6 \text{ Log } [Na+] + 0.41(\% \ G+C) - 0.63(\% \text{ formamide}) - 600/\#bp \text{ in duplex}$$

As an illustration of the above formula, using [Na+]= [0.368] and 50% formamide, with GC content of 42% and an average probe size of 200 bases, the $T_m$ is 57"C. The $T_m$ of a DNA duplex decreases by 1-1.5"C with every 1% decrease in homology. Thus, targets with greater than about 75% sequence identity would be observed using a hybridization temperature of 42"C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains between 10-25, 15-50 and 15 to 100 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically. Nucleic acid sequences comprising single nucleotide polymorphisms have been assembled in the dbSNP database, designated by "rs" numbers. Typing the rs number into the database search box reveals sequences which provide the SNP variation at a specified nucleic acid position in the affected gene. Such nucleic acids can be detectably labeled with non-naturally occurring labels and used to advantage as probes or primers to identify genetic variants in nucleic acids samples isolated from patients.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25, 15-35, 10-40 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

An "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNAs of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting AID mRNA, for example, may be between 15-35 nucleotides in length, and more typically about 21 nucleotides in length.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together. When cloning a genetic region containing a duplication or a deletion, the skilled artisan is well aware that flanking sequences upstream and downstream of the affected region of a suitable length would be employed in the cloning process. Such vectors would have utility, for example in cell lines for studying the effects such alterations have on the encoded proteins.

Many techniques are available to those skilled in the art to facilitate transformation, transfection, or transduction of the expression construct into a prokaryotic or eukaryotic organism. The terms "transformation," "transfection," and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the AID specific marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the AID specific marker encoding nucleic acid. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism," or "transgenic organism" refer to organisms that have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) that have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long. Typically, one or both members of a specific binding pair will comprise a non-naturally occurring detectable label.

"Sample" or "patient sample" or "biological sample" generally refers to a sample which may be tested for a particular molecule, such as an AID specific marker molecule, such as a marker shown in the tables provided below. Samples may include but are not limited to cells, body fluids, including blood, serum, plasma, urine, saliva, tears, pleural fluid and the like.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule which exhibits the capacity to modulate the activity of the SNP containing nucleic acids described herein or their encoded proteins. Agents are evaluated for potential biological activity by inclusion in screening assays described hereinbelow.

A "patient" or "subject" as referred to herein may be either an adult (18 or older) or a pediatric subject (under 18). These two terms are generally used interchangeably herein.

"Treatment," as used herein, covers any administration or application of a therapeutic for a disease (also referred to herein as a "disorder" or a "condition") in a mammal, including a human, and includes inhibiting the disease or progression of the disease, inhibiting or slowing the disease or its progression, arresting its development, partially or fully relieving the disease, partially or fully relieving one or more symptoms of a disease, or restoring or repairing a lost, missing, or defective function; or stimulating an inefficient process.

The term "effective amount" or "therapeutically effective amount" refers to an amount of a drug effective for treatment of a disease or disorder in a subject, such as to partially or fully relieve one or more symptoms. In some embodiments, an effective amount refers to an amount effective, at dosages and for periods of time necessary, to achieve the desired therapeutic or prophylactic result.

Identification of Genetic Alterations

In some embodiments, a subject, or a biological sample from a subject, is assayed to determine the presence or absence of genetic alteration(s) in a DcR3 network gene or their protein sequences, such as in the TNFRSF6B locus or in the DcR3 protein sequence. In some embodiments, the genetic alteration is associated with enhanced activity of genes such as DR3, TL1A, LIGHT, FasL, or their receptors, or with reduced activity of DcR3. In some embodiments, the genetic alteration is associated with increased inflammatory activities such as increased T cell activity or increased production of IFN-gamma.

In some embodiments, information regarding whether a patient has a genetic alteration in a DcR3 network gene or its protein sequence is analyzed, and treatment is initiated based upon this information.

In some embodiments, a DcR3 genetic alteration is associated with reduced levels or activity of DcR3, for example, in some embodiments it is associated with reduced secretion of DcR3 out of the cell, i.e. is a secretion defective alteration, while in other embodiments the alteration results in reduced expression of DcR3 or decreased ligand binding. Thus, in some embodiments, the methods encompass determining whether a subject has a genetic alteration that is associated with reduced DcR3 levels or activity, such as reduced secretion of DcR3, reduced expression of DcR3, or reduced ligand binding activity of DcR3.

DcR3 is expressed to high levels when transiently transfected into 293T cells. In some embodiments, to determine whether an alteration is present that causes a secretion defective DcR3 phenotype, one may assay the amount of DcR3 in 293T cell tissue culture supernatant using, for example, a sandwich ELISA (e.g., R & D Systems DuoSet) as a means of determining whether such supernatant levels are reduced. A quantitative fluorescent Western blot (e.g. LI-COR Odyssey) may be used to assay the total intracellular DcR3, and to normalize those levels against a housekeeping loading control such as β-actin.

Example III below provides a list of SNVs in DcR3 and other DcR3 network genes that are enriched at least 2-fold in pediatric IBD cases compared to controls. In some embodiments, the subject may harbor one or more of those genetic alterations. In some embodiments, a subject may have one or more of the following DcR3 mutations in comparison to the wild-type DcR3 sequence of SEQ ID NO:1: Gly6Arg, Pro23Leu, Gly29Arg, Ala102Thr, Arg103Gln, Arg116His, Gly124Val, Arg172His, Gly178Asp, Gly178Glu, Cys211Gly, Val215Ile, Ala220Val, Arg258Cys, Arg281Cys, or Val282Met. In some embodiments, the DcR3 mutation may be one identified as secretion defective, such as Gly29Arg, Arg116His, Arg172His, Gly178Glu or Asp, Cys211Gly, or Arg258Cys. In other embodiments, the DcR3 mutation may be one identified as secretion normal such as Gly6Arg, Pro23Leu, Ala102Thr, Arg103Gln, Val215Ile, Ala220Val, or Val282Met. In such cases, the DcR3 mutation might have other effects on DcR3 function such as a reduced affinity for one or more ligands.

In some embodiments, a genetic alteration in a DcR3 network gene, such as in TNFRSF6B, may be detected at the DNA level. For example, alterations in the TNFRSF6B locus have been identified in SNP analyses using the SNPs rs2315008, rs4809330, and rs2738774. For instance, allelic variants in TNFRSF6B have been identified in which position 61814400 of rs2315008 is a T and in which position 61820030 of rs4809330 is an A and these mutants have been correlated with an increased risk of IBD. (See Table 1 of WO2009/105590.) Allelic variants in other DcR3 network genes are also provided in the tables of Example III below. Methods of detecting mutations at the DNA level, for example, include in situ hybridization, Southern hybridization, and PCR-based methods. In some embodiments, an SNP analysis may be combined with PCR amplification, for example.

In some embodiments, genetic alterations that affect secretion or expression of DcR3 may be detected through indirect means, such as by examining the level of DcR3 mRNA or protein in a bodily fluid. For instance, assays may be conducted with a variety of samples such as blood, urine, serum, and gastric lavage bodily fluid samples and cell samples such as white blood cells or mononuclear cells.

Methods of Identifying Genetic Alterations in TNFRSF6B or Other Network Genes

In some embodiments a genetic alteration in a DcR3 network gene, such as TNFRSF6B may be detected at the nucleic acid level. Any biological sample may be used, including, but not limited to, blood, urine, serum, gastric lavage, CNS fluid, any type of cell (such as brain cells, white blood cells, mononuclear cells) or body tissue. Any biological source material whereby DNA can be extracted may be used. Samples may be freshly collected, or samples may have been previously collected for any use/purpose and stored until the time of testing for genetic alterations. DNA that was previously purified for a different purpose may also be used.

Standard molecular biology methodologies such as quantitative polymerase chain reaction (PCR), droplet PCR, and TaqMan probes (i.e., hydrolysis probes designed to increase the specificity of quantitative PCR), for example, coupled with sequencing, can be used to assess genetic alterations in a gene. Fluorescent in situ hybridization (FISH) probes may also be used to evaluate genetic alterations.

Various other methods for determining genetic alterations are known, including the following below, some of which may be useful when looking for alterations in additional genes as well as in TNFRSF6B.

Single Nucleotide Variation (SNV)/Single Nucleotide Polymorphism (SNP) Genotyping Determining whether a patient has a genetic alteration in a gene may be done by SNV/SNP Genotyping, using a SNV/SNP genotyping array such as those commercially available from Illumina or Affymetrix. A "single nucleotide variation (SNV)," also interchangeably referred to as a "single nucleotide polymorphism (SNP)" herein, refers to a change in which a single base in the DNA differs from the usual base at that position.

In SNV genotyping, SNVs can be determined by hybridizing complementary DNA probes to the SNV site. A wide range of platforms can be used with SNV genotyping tools to accommodate varying sample throughputs, multiplexing capabilities, and chemistries. In high-density SNV arrays, hundreds of thousands of probes are arrayed on a small chip, such that many SNVs can be interrogated simultaneously when target DNA is processed on the chip. By determining the amount of hybridization of target DNA in a sample to a probe (or redundant probes) on the array, specific SNV alleles can be determined. Use of arrays for SNV genotyping allows the large-scale interrogation of SNVs.

When analyzing CNVs, after SNVs have been analyzed, a computer program must be used to manipulate the SNV data to arrive at CNV data. PennCNV or a similar program, can then be used to detect signal patterns across the genome and identify consecutive genetic markers with copy number changes. (See Wang K. and Bucan M. (June 2008) *Cold Spring Harb Protoc Vol.* 3(6); doi10: 1101/pdb.top46). PennCNV allows for kilobase-resolution detection of CNVs. (See Wang K, et al. (November 2007) *Genome Res.* 17(11): 1665-74).

In CNV analysis, the SNV genotyping data is compared with the behavior of normal diploid DNA. The software uses SNV genotyping data to determine the signal intensity data and SNV allelic ratio distribution and then uses these data to identify deviations from the normal diploid condition of DNA, indicative of the presence of a CNV. This is done in part by using the log R Ratio (LRR), which is a normalized measure of the total signal intensity for the two alleles of the SNV (Wang 2008). If the software detects regions of contiguous SNVs with intensity (LRR) trending below 0, this indicates a CNV deletion. If the software instead detects regions of contiguous SNVs with intensity (LRR) trending above 0, this indicates a CNV duplication. If no change in LRR is observed compared to the behavior of diploid DNA, the sequence is in the normal diploid state with no CNV present. The software also uses B allele frequency (BAF), a normalized measure of the allelic intensity ratio of two alleles that changes when alleles are lost or gained as with a CNV deletion or duplication. For example, a CNV deletion is indicated by both a decrease in LRR values and a lack of heterozygotes in BAF values. In contrast, a CNV duplication is indicated by both an increase in LRR values and a splitting of the heterozygous genotype BAF clusters into two distinct clusters. The software automates the calculation of LRR and BAF to detect CNV deletions and duplications for whole-genome SNV data. The simultaneous analysis of intensity and genotype data accurately defines the normal diploid state and determines CNVs.

Array platforms such as those from Illumina, Affymetrix, and Agilent may be used in SNV Genotyping. Custom arrays may also be designed and used based on the data described herein.

Comparative Genomic Hybridization

Comparative genomic hybridization (CGH) is another method that may be used to evaluate genetic alterations. CGH is a molecular cytogenetic method for analyzing genetic alterations in comparison to a reference sample using competitive fluorescence in situ hybridization (FISH). DNA is isolated from a patient and a reference source and independently labeled with fluorescent molecules (i.e., fluorophores) after denaturation of the DNA. Hybridization of the fluorophores to the resultant samples is compared along the length of each chromosome to identify chromosomal differences between the two sources. A mismatch of colors indicates a gain or loss of material in the test sample in a specific region, while a match of the colors indicates no difference in genetic alterations such as copy number between the test and reference samples at a particular region.

Sequencing Methods

Whole genome sequencing, whole exome sequencing, or targeted sequencing may also be used to analyze genetic alterations in multiple genes. Whole genome sequencing (also known as full genome sequencing, complete genome sequencing, or entire genome sequencing) involves sequencing of the full genome of a species, including genes that do or do not code for proteins. Whole exome sequencing, in contrast, is sequencing of only the protein-coding genes in the genome (approximately 1% of the genome). Targeted sequencing involves sequencing of only selected parts of the genome.

A wide range of techniques would be known to those skilled in the art to perform whole genome, whole exome, or targeted sequencing with DNA purified from a subject. Similar techniques could be used for different types of sequencing. Techniques used for whole genome sequencing include nanopore technology, fluorophore technology, DNA nanoball technology, and pyrosequencing (i.e., sequencing by synthesis). In particular, next-generation sequencing (NGS) involves sequencing of millions of small fragments of DNA in parallel followed by use of bioinformatics analyses to piece together sequencing data from the fragments.

As whole exome sequencing does not need to sequence as large an amount of DNA as whole genome sequencing, a wider range of techniques are may be used. Methods for whole exome sequencing include polymerase chain reaction methods, NGS methods, molecular inversion probes, hybrid capture using microarrays, in-solution capture, and classical Sanger sequencing. Targeted sequencing allows for providing sequence data for specific genes rather than whole genomes and can use any of the techniques used for other types of sequencing, including specialized microarrays containing materials for sequencing genes of interest. Proprietary methodologies, such as those from BioNano or OpGen, using genome mapping technology can also be used to evaluate genetic alterations.

Treatment of Autoimmune Disease Patients Harboring DcR3-Related Genetic Alterations with DcR3 Ligand Inhibitors This disclosure encompasses methods of treating autoimmune diseases with a DcR3 ligand inhibitor, such as a FasL, TL1A, or LIGHT inhibitor, such as a FasL, TL1A, or LIGHT antagonist antibody. In some embodiments, the subject being treated harbors at least one TNFRSF6B gene alteration, or harbors at least one mutation in DcR3 or a DcR3 network protein. In some embodiments, the subject is heterozygous or homozygous for such an alteration, such as an alteration that reduces secretion, expression, or ligand binding activity of DcR3. In some embodiments, the subject harbors at least one genetic alteration in another DcR3 network gene.

In some embodiments, the autoimmune disease is one or more of ankylosing spondylitis (AS), psoriasis (PS or PSOR), celiac disease (CEL), systemic lupus erythematosus (SLE), common variable immunodeficiency (CVID), inflammatory bowel disease (IBD) ulcerative colitis (UC), type I diabetes (T1D), juvenile idiopathic arthritis (JIA), Crohn's disease (CD), alopecia areata (AA), multiple sclerosis (MS), primary biliary cirrhosis (PBC), primary sclerosing cholangitis (PSC), rheumatoid arthritis (RA), Sjogren's syndrome (SJO), systemic sclerosis (SSC), spondyoarthropathy (SPA), vitiligo (VIT), asthma, or thyroiditis (AITD, THY or TH). In some embodiments, the subject to be treated is hypo-responsive to TNF alpha monoclonal antibody therapy. In some embodiments, the subject has developed or is developing resistance to TNF alpha monoclonal antibody therapy. In some embodiments, the autoimmune disease is a pediatric form of any one or more of the above.

In some embodiments, the methods encompass determining whether the patient has a genetic alteration in the TNFRSF6B locus and, if an alteration is detected, treating the patient with a DcR3 ligand inhibitor.

In some embodiments, the DcR3 ligand inhibitor is a small molecule, while in other embodiments the inhibitor is a biologic, such as an antibody, a ligand trap such as a soluble peptide comprising a domain of a DcR3 pathway protein, an aptamer, or a nucleic acid such as a small inhibiting RNA (siRNA) or antisense nucleic acid. In some embodiments, the DcR3 ligand inhibitor is an antibody, such as an antagonist antibody of FasL, LIGHT, or TL1A. In some embodiments, the DcR3 ligand inhibitor is not an inhibitor of TL1A. In some embodiments, the DcR3 ligand inhibitor is not an inhibitor of FasL.

Some FasL inhibitors currently in development include, for instance, APG 101 (apocept) (Apogenix GmbH), APG 103, KAHR 102, KAHR 103 (KAHR Medical), and MFas-L (Memgen LLC).

In some embodiments, the DcR3 ligand inhibitor is an antibody antagonist of LIGHT (i.e. an anti-LIGHT antibody). Suitable anti-LIGHT antibodies for the present treatment methods include those described, for example, in WO 2008/027338, US20130315913, US20130323240, and WO 2015/107331, which are incorporated herein by reference in their entirety. In some embodiments, the anti-LIGHT antibody inhibits a biological function of LIGHT, such as binding to one of its ligands, such as HVEM or LTβR.

DcR3 ligand inhibitors may be administered systemically in parenteral, oral solid and liquid formulations, ophthalmic, suppository, aerosol, topical or other similar formulations. In addition to the appropriate active ingredient, such as a DcR3 ligand inhibitor, an appropriate pharmaceutical composition may contain pharmaceutically-acceptable carriers and other ingredients known to enhance and facilitate drug administration. Thus such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the active ingredient to a patient according to the methods of the invention. The use of nanoparticles to deliver siRNAs or expression vectors, as well as cell membrane permeable peptide carriers that can be used are described in Crombez et al., Biochemical Society Transactions v35:p44 (2007).

Anti-LIGHT Antibodies

In some embodiments, the DcR3 ligand inhibitor is an anti-LIGHT antibody. The anti-LIGHT antibody may comprise the CDR sequences of the E1, E13, E63, F19, or F23 antibodies, which are provided in WO 2008/027338 and U.S. Pat. Nos. 8,058,402 B2, 8,461,307 B2, and 8,974,787 B2, each of which is incorporated herein by reference.

In some embodiments, the anti-LIGHT antibody comprises a heavy chain comprising three CDR sequences comprising each of SEQ ID NOs: 2, 3, and 4, respectively. In some embodiments, the anti-LIGHT antibody comprises a light chain comprising three CDR sequences comprising each of SEQ ID NOs: 5, 6, and 7, respectively. In some embodiments, the antibody comprises a heavy chain and a light chain, the heavy chain comprising three CDR sequences comprising each of SEQ ID NOs: 2, 3, and 4, respectively, and the light chain comprising three CDR sequences comprising each of SEQ ID NOs: 5, 6, and 7, respectively.

In some embodiments, the anti-LIGHT antibody comprises a heavy chain variable region sequence comprising SEQ ID NO: 8 or that is at least 85%, at least 90%, at least 95%, at least 98%, or at least 99% identical to SEQ ID NO:8. In some embodiments, the anti-LIGHT antibody comprises a light chain variable region sequence comprising SEQ ID NO:9 or that is at least 85%, at least 90%, at least 95%, at least 98%, or at least 99% identical to SEQ ID NO:9. In some embodiments, the anti-LIGHT antibody comprises a heavy chain comprising SEQ ID NO: 8 or that is at least 85%, at least 90%, at least 95%, at least 98%, or at least 99% identical to SEQ ID NO:8. In some embodiments, the anti-LIGHT antibody comprises a light chain comprising SEQ ID NO:9 or that is at least 85%, at least 90%, at least 95%, at least 98%, or at least 99% identical to SEQ ID NO:9. In some embodiments, the anti-LIGHT antibody comprises both a heavy chain comprising SEQ ID NO: 8 or that is at least 85%, at least 90%, at least 95%, at least 98%, or at least 99% identical to SEQ ID NO:8 and a light chain comprising SEQ ID NO:9 or that is at least 85%, at least 90%, at least 95%, at least 98%, or at least 99% identical to SEQ ID NO:9.

In some embodiments, the anti-LIGHT antibody comprises a heavy chain comprising three CDR sequences comprising each of SEQ ID NOs: 10, 11, and 12, respectively. In some embodiments, the anti-LIGHT antibody comprises a light chain comprising three CDR sequences comprising each of SEQ ID NOs: 13, 14, and 15, respectively. In some embodiments, the antibody comprises a heavy chain and a light chain, the heavy chain comprising three CDR sequences comprising each of SEQ ID NOs: 10, 11, and 12, respectively, and the light chain comprising three CDR sequences comprising each of SEQ ID NOs: 13, 14, and 15, respectively.

In some embodiments, the anti-LIGHT antibody comprises a heavy chain comprising three CDR sequences comprising each of SEQ ID NOs: 16, 17, and 18, respectively. In some embodiments, the anti-LIGHT antibody comprises a light chain comprising three CDR sequences comprising each of SEQ ID NOs: 19, 20, and 21, respectively. In some embodiments, the antibody comprises a heavy chain and a light chain, the heavy chain comprising three CDR sequences comprising each of SEQ ID NOs: 16, 17, and 18, respectively, and the light chain comprising three CDR sequences comprising each of SEQ ID NOs: 19, 20, and 21, respectively.

In some embodiments, the anti-LIGHT antibody comprises a heavy chain comprising three CDR sequences comprising each of SEQ ID NOs: 22, 23, and 24, respectively. In some embodiments, the anti-LIGHT antibody comprises a light chain comprising three CDR sequences comprising each of SEQ ID NOs: 25, 26, and 27, respectively. In some embodiments, the antibody comprises a heavy chain and a light chain, the heavy chain comprising three CDR sequences comprising each of SEQ ID NOs: 22, 23, and 24, respectively, and the light chain comprising three CDR sequences comprising each of SEQ ID NOs: 25, 26, and 27, respectively.

In some embodiments, the anti-LIGHT antibody comprises a heavy chain comprising three CDR sequences comprising each of SEQ ID NOs: 28, 29, and 30, respectively. In some embodiments, the anti-LIGHT antibody comprises a light chain comprising three CDR sequences comprising each of SEQ ID NOs: 31, 32, and 33, respectively. In some embodiments, the antibody comprises a heavy chain and a light chain, the heavy chain comprising three CDR sequences comprising each of SEQ ID NOs: 28, 29, and 30, respectively, and the light chain comprising three CDR sequences comprising each of SEQ ID NOs: 31, 32, and 33, respectively.

In some embodiments, the anti-LIGHT antibody comprises a heavy chain comprising three CDR sequences comprising each of SEQ ID NOs: 34, 35, and 36, respectively. In some embodiments, the anti-LIGHT antibody comprises a light chain comprising three CDR sequences comprising each of SEQ ID NOs: 37, 38, and 39, respectively. In some embodiments, the antibody comprises a heavy chain and a light chain, the heavy chain comprising three CDR sequences comprising each of SEQ ID NOs: 34, 35, and 36, respectively, and the light chain comprising three CDR sequences comprising each of SEQ ID NOs: 37, 38, and 39, respectively.

In some embodiments, the anti-LIGHT antibody comprises a heavy chain comprising three CDR sequences comprising each of SEQ ID NOs: 40, 41, and 42, respectively. In some embodiments, the anti-LIGHT antibody comprises a light chain comprising three CDR sequences comprising each of SEQ ID NOs: 43, 44, and 45, respectively. In some embodiments, the antibody comprises a heavy chain and a light chain, the heavy chain comprising three CDR sequences comprising each of SEQ ID NOs: 40, 41, and 42, respectively, and the light chain comprising three CDR sequences comprising each of SEQ ID NOs: 43, 44, and 45, respectively.

In some embodiments, the anti-LIGHT antibody comprises a heavy chain comprising three CDR sequences comprising each of SEQ ID NOs: 46, 47, and 48, respectively. In some embodiments, the anti-LIGHT antibody comprises a light chain comprising three CDR sequences comprising each of SEQ ID NOs: 49, 50, and 51, respectively. In some embodiments, the antibody comprises a heavy chain and a light chain, the heavy chain comprising three CDR sequences comprising each of SEQ ID NOs: 46, 47, and 48, respectively, and the light chain comprising three CDR sequences comprising each of SEQ ID NOs: 49, 50, and 51, respectively.

In some embodiments, the anti-LIGHT antibody may comprise the CDR sequences of the antibodies, which are described in US2013/0323240 and U.S. Pat. No. 8,524,869 B2, which are incorporated herein by reference. For example, in some embodiments, the anti-LIGHT antibody comprises a heavy chain comprising three CDR sequences comprising each of SEQ ID NOs: 52, 53, and 54, respectively. In some embodiments, the anti-LIGHT antibody comprises a light chain comprising three CDR sequences comprising each of SEQ ID NOs: 55, 56, and 57, respectively. In some embodiments, the antibody comprises a heavy chain and a light chain, the heavy chain comprising three CDR sequences comprising each of SEQ ID NOs: 52, 53, and 54, respectively, and the light chain comprising three CDR sequences comprising each of SEQ ID NOs: 55, 56, and 57, respectively.

In some embodiments, the anti-LIGHT antibody comprises a heavy chain variable region sequence comprising SEQ ID NO:58 or that is at least 85%, at least 90%, at least 95%, at least 98%, or at least 99% identical to SEQ ID NO:58. In some embodiments, the anti-LIGHT antibody comprises a light chain variable region sequence comprising SEQ ID NO:59 or that is at least 85%, at least 90%, at least 95%, at least 98%, or at least 99% identical to SEQ ID NO:59. In some embodiments, the anti-LIGHT antibody comprises a heavy chain comprising SEQ ID NO:58 or that is at least 85%, at least 90%, at least 95%, at least 98%, or at least 99% identical to SEQ ID NO:58. In some embodiments, the anti-LIGHT antibody comprises a light chain comprising SEQ ID NO:59 or that is at least 85%, at least 90%, at least 95%, at least 98%, or at least 99% identical to SEQ ID NO:59. In some embodiments, the anti-LIGHT antibody comprises both a heavy chain comprising SEQ ID NO:58 or that is at least 85%, at least 90%, at least 95%, at least 98%, or at least 99% identical to SEQ ID NO:58 and a light chain comprising SEQ ID NO:59 or that is at least 85%, at least 90%, at least 95%, at least 98%, or at least 99% identical to SEQ ID NO:59.

In some embodiments, the anti-LIGHT antibody may comprise a heavy chain and a light chain together comprising one of the following sets of CDR-H1, CDR-H2, CDR-H3, CDR-L1, CDR-L2, and CDR-L3 sequences described in the sequence listing from US2013/0323240: SEQ ID NOs: 18, 19, 20 and SEQ ID NOs: 38, 41, 42 of US2013/0323240; SEQ ID NOs: 18, 19, 21 and SEQ ID NOs: 39, 41, 42 of US2013/0323240; SEQ ID NOs: 18, 19, 22 and SEQ ID NOs: 40, 41, 42 of US2013/0323240; SEQ ID NOs: 23, 24, 25 and SEQ ID NOs: 43, 44, 45 of US2013/0323240; SEQ ID NOs: 26, 27, 28 and SEQ ID NOs: 46, 47, 48 of US2013/0323240; SEQ ID NOs: 29, 30, 31 and SEQ ID NOs: 49, 50, 51 of US2013/0323240; SEQ ID NOs: 32, 33, 34 and SEQ ID NOs: 52, 53, 54 of US2013/0323240; and SEQ ID NOs: 35, 36, 37 and SEQ ID NOs: 55, 50, 51 of US2013/0323240.

In some embodiments, the anti-LIGHT antibody comprises the CDR sequences of the 18E04, 98C07, 1C02, 1C06, 13H04, 31A10, 98C07, 42A02, 29C02, 14B09, 117C06, 114F05, and 62C01 antibodies described in WO 2015/107331, which is also incorporated by reference herein.

For example, in some embodiments, the anti-LIGHT antibody comprises a heavy chain comprising three CDR sequences comprising each of SEQ ID NOs: 60, 61, and 62, respectively. In some embodiments, the anti-LIGHT antibody comprises a light chain comprising three CDR sequences comprising each of SEQ ID NOs: 63, 64, and 65, respectively. In some embodiments, the antibody comprises a heavy chain and a light chain, the heavy chain comprising three CDR sequences comprising each of SEQ ID NOs: 60, 61, and 62, respectively, and the light chain comprising three CDR sequences comprising each of SEQ ID NOs: 63, 64, and 65, respectively.

In some embodiments, the anti-LIGHT antibody comprises a heavy chain comprising three CDR sequences comprising each of SEQ ID NOs: 66, 67, and 68, respectively. In some embodiments, the anti-LIGHT antibody comprises a light chain comprising three CDR sequences comprising each of SEQ ID NOs: 69, 70, and 71, respectively. In some embodiments, the antibody comprises a heavy chain and a light chain, the heavy chain comprising three CDR sequences comprising each of SEQ ID NOs: 66, 67, and 68, respectively, and the light chain comprising three CDR sequences comprising each of SEQ ID NOs: 69, 70, and 71, respectively.

In some embodiments, the anti-LIGHT antibody comprises a heavy chain comprising three CDR sequences comprising each of SEQ ID NOs: 72, 73, and 74, respectively. In some embodiments, the anti-LIGHT antibody comprises a light chain comprising three CDR sequences comprising each of SEQ ID NOs: 75, 76, and 77, respectively. In some embodiments, the antibody comprises a heavy chain and a light chain, the heavy chain comprising three CDR sequences comprising each of SEQ ID NOs: 72, 73, and 74, respectively, and the light chain comprising three CDR sequences comprising each of SEQ ID NOs: 75, 76, and 77, respectively.

In some embodiments, the anti-LIGHT antibody comprises a heavy chain comprising three CDR sequences comprising each of SEQ ID NOs: 78, 79, and 80, respectively. In some embodiments, the anti-LIGHT antibody comprises a light chain comprising three CDR sequences comprising each of SEQ ID NOs: 81, 82, and 83, respectively. In some embodiments, the antibody comprises a heavy chain and a light chain, the heavy chain comprising three CDR sequences comprising each of SEQ ID NOs: 78, 79, and 80, respectively, and the light chain comprising three CDR sequences comprising each of SEQ ID NOs: 81, 82, and 83, respectively.

Additional DcR3 Ligand Inhibitors

In some embodiments, the DcR3 ligand inhibitor may be a nucleic acid molecule, such as an siRNA that inhibits the expression of an AID-associated mRNA. For example, an siRNA may be used to target DcR3 ligands as a means of downregulation of those ligands. An siRNA can be delivered to a patient in vivo either systemically or locally with carriers, as discussed below. The compositions of the invention may be used alone or in combination with other agents or genes encoding proteins to augment the efficacy of the compositions. There are several ways to administer the siRNA of the invention in vivo to treat an AID including, but not limited to, naked siRNA delivery, siRNA conjugation and delivery, liposome carrier-mediated delivery, polymer carrier delivery, nanoparticle compositions, plasmid-based methods, and the use of viruses.

siRNA composition of the invention can comprise a delivery vehicle, including liposomes, for administration to a subject, carriers and diluents and their salts, and/or can be present in pharmaceutically acceptable formulations. This can be necessary to allow the siRNA to cross the cell membrane and escape degradation. Methods for the delivery of nucleic acid molecules are described in Akhtar et al., 1992, Trends Cell Bio., 2, 139; Delivery Strategies for Antisense Oligonucleotide Therapeutics, ed. Akhtar, 1995, Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192; Beigelman et al., U.S. Pat. No. 6,395,713 and Sullivan et al., PCT WO 94/02595 further describe the general methods for delivery of nucleic acid molecules.

In other approaches, it may be desirable to increase expression levels of wild type proteins lacking the genetic variation described herein. In this approach, vectors encoding the wild type DcR3 protein would be introduced into target cells. Such vectors include without limitation, adenoviral vectors, adeno-associated viral vectors, and lentiviral vectors etc.

In some embodiments, the DcR3 ligand inhibitor may be a ligand trap. As DcR3 itself acts to inhibit the immune-stimulating activity of ligands such as LIGHT or TL1A when it binds to these ligands, in some embodiments, the ligand trap may be based on DcR3 itself, such as DcR3, a DcR3 fusion molecule, or a DcR3 aptamer.

Effects of DCR3 Genetic Alterations on the Cytotoxic Effects of DCR3 Ligand FasL Immuno-modulation mediated by DcR3 in EBV (Epstein-Barr virus) transformed cell lines from IBD patients with and without genetic alterations in TNFRSF6B (from the SNP rs2315008) was conducted as described in Example I below. EBV cell lines from IBD patients harboring alterations in the TNFRSF6B gene may exhibit a differential pattern of DcR3 expression and NF-κB activation that may promote inflammation in IBD subjects. The results suggest that pathogenic inflammation in IBD may in part be the result of non-canonical developmental signals impinging on a NF-κB signaling.

For example, patient EBV cells with heterozygous TNFRSF6B gene alterations may exhibit more aggressive inflammatory marker upregulation in this experimental model compared to cells without such mutations. The experiments examined whether these EBV cells benefit from knockdown of DcR3 expression with a DCR3 siRNA. Cells receiving DcR3 siRNA along with a soluble FasL construct (sFasL) showed a decrease in cell growth in comparison to cells receiving a control siRNA (CsiRNA) and sFasL. These results suggest that siRNA knockdown of DcR3 expression enhances the cytototoxic effects of FasL.

Treatment of Autoimmune Disease Patients Harboring DcR3 Genetic Alterations with NF-κB Inhibitors The above results suggest that influencing the non-canonical NF-κB pathway may also be a way to treat autoimmune disease patients harboring a genetic alteration in a DcR3 network protein, such as an alteration associated with reduced expression, secretion, or ligand binding of DcR3.

In some embodiments, an NF-κB inhibitor may be selected from a molecule that targets the non-canonical NF-κB pathway, such as the NF-κB activators RANKL or BAFF, such as a RANKL inhibitor such as denosumab. Other molecules that may impact NF-κB activity include small molecules such as andrographolide, bardoxolone methyl, copper gluconate, curcurmin, declopramide, dexlipotam, disulfiram, docosahexanoic acid, menadione sodium bisulfite, mesalamine, oleandrin, omaveloxolone, orazipone, perflubron, pyridyl cyanoguanidine, tarenflurbil, and tyloxapol. Other NF-κB influencing molecules in development include 4SC301 (Takeda), ACU-D1 (Accuitis), AMG0101, MP40, MP41, and MP42 (Shionogi), C150 (Avidin Ltd.), CAT1002, CAT1004, CAT1040, and CAT4001 (Catabasis Pharmaceuticals), CHS828 and OSH101 (LEO Pharma), CIGN 552 (Centro de Ingenieria Genetica y Biotecnologia), CXS2101 (ChemGenex Pharmaceuticals), DA9201 (Dong-A Socio Holdings), DP 155 (D-Pharm Ltd.), EC 70124 (EntreChem SL), FY101C and FY103B (FyMed Inc.), GTx 186 (GTx Inc.), HE 3177 and RE 3413 and HE 3286 (Harbor Therapeutics), HMPL 004 and HMPL 010 (Hutchison), IMD 0560 (IMMD Inc.), INV 404 and INV 405 (InVase Therapeutics), AVE 0547 (Sanofi), IRFI 042 (Biomedica Foscama Group), MCL 0071 (Malvern Cosmeceutics Ltd.), MRx 102 (MyeloRx LLC), NPI1342 and NPI1387 (Nereus Pharmaceuticals), OR1384 (Orion Corp.), AQP1639 (Aquapharm Biodiscovery Ltd.), PBI1308 (ProMetric Life Sci.), PF 184 (Pfizer), PPL003 (Portage Biotech Inc.), PBS1086 (Profectus BioSciences), SC71570 (4SC AG), WAY 204688 (Wyeth), TG1060 (TG Biotech Co. Ltd.), TX153 (OXIS Intl.), VBP 15 (ReveraGen), and GIT 027 (Ganial).

Kits and Articles of Manufacture

Any of the aforementioned products can be incorporated into a kit which may contain an AID-associated SNP specific marker polynucleotide or one or more such markers immobilized on a Gene Chip, an oligonucleotide, a polypeptide, a peptide, an antibody, one or more non-naturally occurring detectable labels, marker, or reporter, a pharmaceutically acceptable carrier, a physiologically acceptable carrier, instructions for use, a container, a vessel for administration, an assay substrate, or any combination thereof.

Use of AID-Associated SNPs for Developing Further Therapeutic Agents

Certain SNPs have been associated with the etiology of AIDs involving the DcR3 signaling pathway. Thus, methods for identifying agents that modulate activity of genes and their encoded products containing such SNPs in the DcR3 network may result in the generation of efficacious therapeutic agents for the treatment of AID, in certain embodiments, pAID.

The chromosomal regions described herein contain protein coding regions which provide suitable targets for the rational design of therapeutic agents which modulate their activity. Small peptide molecules corresponding to these regions may be used to advantage in the design of therapeutic agents which effectively modulate the activity of the encoded proteins.

Molecular modeling may facilitate the identification of specific organic molecules with capacity to bind to the active site of the proteins encoded by the SNP containing nucleic acids based on conformation or key amino acid residues required for function. A combinatorial chemistry approach can be used to identify molecules with greatest activity and then iterations of these molecules can be developed for further cycles of screening. In certain embodiments, candidate drugs can be screened from large libraries of synthetic or natural compounds. One example is an FDA approved library of compounds that can be used by humans. In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd. (Moscow, Russia), Princeton Biomolecular (Monmouth Junction, N.J.), Scientific Exchange (Center Ossipee, N.H.), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China).

Libraries of natural compounds in the form of bacterial, fungal, plant and animal extracts are commercially available or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Several commercial libraries can be used in the screens.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as airway smooth muscle cells) which have a non-functional or altered AID associated gene. These host cell lines or cells are defective at the polypeptide level. The host cell lines or cells are grown in the presence of drug compound. For example, when the AID is asthma, the rate of constriction or relaxation of the host cells is measured to determine if the compound is capable of regulating the airway responsiveness in the defective cells.

Host cells contemplated for use in the present invention include but are not limited to bacterial cells, T cells, B cells, macrophage cells, dendritic cells, epithelial cells, fungal cells, insect cells, and any suitable type of mammalian cell. The AID-associated SNP encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein. In certain embodiments, nucleic acids in appropriate expression vectors are introduced into target cells in cases where the genetic variation is associated with a loss of beneficial function and increasing the cellular level of proteins lacking the genetic variation would be therapeutically efficacious.

A wide variety of expression vectors are available that can be modified to express the novel DNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/ V5 & His (Invitrogen); and yeast vectors such as YRP17, YIPS, and YEP24 (New England Biolabs, Beverly, Mass.), as well as pRS403 and pRS413 Stratagene Inc.); retroviral vectors such as PLNCX and pLPCX (Clontech); and adenoviral and adeno-associated viral vectors of different serotypes.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, and *Saccharomyces* promoters such as the gal4 inducible promoter and the PGK constitutive promoter. In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the AID-associated SNPs of the present invention or functional fragments thereof provide a system in which to screen potential compounds or agents for the ability to modulate the development of AID. Thus, in one embodiment, the nucleic acid molecules of the invention may be used to create recombinant cell lines for use in assays to identify agents which modulate aspects of aberrant cytokine signaling associated with AID such as aberrant bronchoconstriction or cellular transport across epithelial membranes for example. Also provided herein are methods to screen for compounds capable of modulating the function of proteins encoded by SNP containing nucleic acids.

Another approach entails the use of phage display libraries engineered to express fragment of the polypeptides encoded by the SNP containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs that have, e.g., improved polypeptide activity or stability or which act as inhibitors, agonists, antagonists, etc. of polypeptide activity. By virtue of the availability of SNP containing nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of AID-associated SNP containing nucleic acids enables the production of strains of laboratory mice carrying the AID-associated SNPs of the invention. Transgenic mice expressing the AID-associated SNP of the invention provide a model system in which to examine the role of the protein encoded by the SNP containing nucleic acid in the development and progression towards AID. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role that a target protein plays in various processes associated with the AID phenotypes. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of AID-associated SNP containing nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated AID-associated SNV/SNP genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Non-homologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes that are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabino-fluranosyl)-5-iodou-racil, (FIAU). By this counter selection, the number of homologous recombinants in the surviving transformants can be increased. Utilizing AID-associated SNP containing nucleic acid as a targeted insertional cassette provides means to detect a successful insertion as visualized, for example, by acquisition of immunoreactivity to an antibody immunologically specific for the polypeptide encoded by AID-associated SNP nucleic acid and, therefore, facilitates screening/selection of ES cells with the desired genotype.

As used herein, a knock-in animal is one in which the endogenous murine gene, for example, has been replaced with human AID-associated SNV/SNP containing gene of the invention. Such knock-in animals provide an ideal model system for studying the development of AID.

As used herein, the expression of an AID-associated SNP containing nucleic acid, fragment thereof, or an AID-associated SNP fusion protein can be targeted in a "tissue specific manner" or "cell type specific manner" using a vector in which nucleic acid sequences encoding all or a portion of AID-associated SNP are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific proteins are well known in the art and described herein.

The nucleic acid sequence encoding the AID-associated SNP of the invention may be operably linked to a variety of different promoter sequences for expression in transgenic animals. Such promoters include, but are not limited to a prion gene promoter such as hamster and mouse Prion promoter (MoPrP), described in U.S. Pat. No. 5,877,399 and in Borchelt et al., Genet. Anal. 13(6) (1996) pages 159-163; a rat neuronal specific enolase promoter, described in U.S. Pat. Nos. 5,612,486, and 5,387,742; a platelet-derived growth factor B gene promoter, described in U.S. Pat. No. 5,811,633; a brain specific dystrophin promoter, described in U.S. Pat. No. 5,849,999; a Thy-1 promoter; a PGK promoter; and a CMV promoter for the expression of transgenes in airway smooth muscle cells.

Methods of use for the transgenic mice of the invention are also provided herein. Transgenic mice into which a nucleic acid containing the AID-associated SNP or its encoded protein have been introduced are useful, for example, to develop screening methods to screen therapeutic agents to identify those capable of modulating the development of AID.

The following examples are provided to illustrate certain embodiments of the invention. They are not intended to limit the invention in any way.

Example I

To better characterize the role of DcR3 variants in IBD, we sequenced the exons of TNFRSF6B in a large number of Caucasian pediatric IBD cases and healthy controls. We uncovered several missense variants at the TNFRSF6B locus, affecting secretion of DcR3 from cultured cells that were significantly enriched in the IBD cases. Since these cytokines are pro-inflammatory, deficiency of DcR3 expression, secretion, or ligand-binding leads to unopposed inflammatory signals and exacerbation of IBD and suggests that DcR3 harboring such variation may be less effective in down-regulating ligands that provoke inflammation in the IBD cases. Thus, DCR3 has multiple complex roles within the innate and adaptive immune system, which may result in a net pro- or anti-inflammatory effect based upon the precise context and further modified by specific sequence variants (Refs. 7, 8).

The role of NF-κB in the pathogenesis of IBD has been examined in recent studies. Colon biopsies from IBD patients with active disease show increased levels of NF-κB p65 protein, which correlates with the severity of intestinal inflammation (9). Aberrant activation of the transcription factor NF-κB controls the expression of many genes of inflammatory cytokines involved in the pathogenesis of IBD (10). Here we describe the immuno-modulatory role of DcR3 in EBV transformed pediatric control and patient-derived cell lines with and without risk variants in TNFRSF6B, best captured by the tagging SNP, rs2315008.

IκBα degradation

The ability of DcR3 to induce IκBα degradation was determined by immunoblot analysis. Briefly, $1 \times 10^6$ cells derived from control and IBD patients EBV transformed cell lines harboring risk variants in TNFRSF6B (A allele) were activated with TNF-α (10 ng/ml) in a time course experiment and used to evaluate the kinetics of IκBα degradation for time points ranging from 0 min to 60 min. Cells were then lysed in NuPAGE LDS sample buffer (Invitrogen Life Technologies) and boiled for 5 min before loading. A total of 10 ug of protein per sample was separated on 4-12% Bis-Tris density gradient gels in MOPS SDS running buffer and transferred to nitrocellulose membrane membranes (Invitrogen Life Technologies), which after blocking with 3% BSA and 0.1% Tween 20 were incubated with rabbit polyclonal anti-IκBαC-21 (Santa Cruz Bio-technology). Bound Ab was detected using HRP-conjugated donkey anti-rabbit (Amersham Biosciences) and ECL detection system (Amersham Biosciences). Where specified, membranes were stripped in 0.2 M glycine (pH 2.5), 0.05% Tween 20, and 140 mM NaCl in TBS at 50° C. for 30 min, blocked with 3% BSA, and reprobed with mouse anti-β-actin monoclonal Ab (Santa Cruz Bio-technology).

NF-κB Kinetics

NF-κB kinetics were determined by immunoblot analysis of cytoplasm and nuclear extracts from cells activated with TNF-α (10 ng/ml) in a time course experiment. Briefly, nuclear extracts were prepared by washing cells twice with 1 ml of ice-cold PBS and resuspended in 400 ul of ice-cold lysis buffer containing 1 M HEPES, 0.5M EDTA, 0.1M EGTA, 2M KCl, 0.1M DTT, mix of protease inhibitors at 5 ug/ml (Roche), and 10% Nonidet P-40 and incubated for 15 min on ice with occasional vortexing to obtain complete cell lysis and release of nuclei. Tubes were centrifuged at 13,400×g for 1 min, supernatant (cytoplasmic extract) was collected and remaining nuclei were resuspended in 25 ul of ice-cold nuclear extraction buffer containing 1 M HEPES, 5 M NaCl, 0.5 M EDTA, 0.1 M DTT, and mixture of protease inhibitors at 5 ug/ml (Roche), incubated for 30 min on ice and centrifuged at 13,400×g for 5 min. Supernatant containing the soluble nuclear proteins was aliquoted in pre-chilled tubes, snap-frozen in liquid nitrogen and stored at −80° C. until use. Equal protein amounts of the extracts (10 ug) as determined using detergent compatible protein assay (Bio-Rad) were used in experiments.

MTT Analysis

The effect of DcR3 on cell proliferation was measured by the colorimetric MTT assay using an MTT (Microtiter-tetrazolium, Sigma, USA) based assay. Briefly, the cells (5,000/ml) were incubated in triplicate in a 96-well plate (Costar, Cambridge, Mass., USA) in a final volume of 0.2 ml for the indicated times. Thereafter, 20 µl of MTT solution (5 g/L) was added to each well and then incubated for 12 h. After centrifugation, the supernatant was removed from each well. The colored formazan crystal produced from MTT was dissolved in 0.15 ml of DMSO and then the optical density (OD) value was measured on a microplate reader. Each experiment was performed in duplicate and repeated five times.

Caspases by Western Blot Analysis

Aliquots (10 µg of protein) of whole cell lysates from TNF-α (10 ng/ml) activated cells in a time course experiment were separated on 4-12% bis-Tris gels, blotted onto a nitrocellulose membrane and probed with antibodies against Caspase-8, Caspase-3, Caspase-9 and Bcl-2 (Sigma, USA). Membranes were washed with 0.05% (vol/vol) Tween 20 in PBS (pH 7.6) and incubated with 1: 10,000 dilution of horseradish peroxides-conjugated secondary Abs for 60 min at room temperature. Bound Ab was detected using ECL detection system (Amersham Biosciences). Where specified, membranes were stripped in 0.2 M glycine (pH 2.5), 0.05% Tween 20, and 140 mM NaCl in TBS at 50° C. for 30 min, blocked with 3% BSA, and reprobed with mouse anti-β-actin monoclonal Ab (Santa Cruz Biotechnology).

siRNA Knockdown of DcR3 Expression

The expression of DcR3 was reduced using siRNAs in the EBV transformed cell lines derived from control and IBD patients harboring risk variants in TNFRSF6B (A allele). Briefly, $3 \times 10^6$ cells were transfected with 100 nM DcR3 siRNA duplexes or with DcR3 non-silence control using Amaxa Nucleofector Kit and program T-20. The siRNA-transfected cells were incubated for 48 h after nucleofection and the degree of knockdown relative to introduction of control siRNA was confirmed by western blot using DcR3 mouse monoclonal antibody (Abgent) on whole cell lysates. The 21-mer siRNAs were synthesized by DHARMACON. The DcR3 siRNA sequences were as follows: sense sequence, 5'-GCC AGG CUC UUC CUC CCA UdTdT-3' (SEQ ID NO: 1); antisense sequence, 5'-AUG GGA GGA AGA GCC UGG CdTdT-3' (SEQ ID NO: 2). The non-silence control siRNA sequences were as follows: sense sequence, 5'-GCC CGC UUU CCC UCA GCA UdTdT-3' (SEQ ID NO: 3); antisense sequence, 5'-AUG CUG AGG GAA AGC GGG C-3 (SEQ ID NO: 4).

Results

DcR3 Expression in EBV Transformed Non-Secretor, Control and Patient Derived Cell Lines Because DcR3 lacks a transmembrane sequence and is a soluble protein, we used an immunoblot assay to determine the expression of DcR3 in whole cell lysates and culture supernatant from control and patient-derived Immortalized cell lines with and without risk variants in the TNF Receptor Superfamily 6B gene using a mouse monoclonal antibody to DcR3. We used a non-secretor cell line as a baseline control for the development of the assay model. As shown in FIG. 1, control and patient homozygous for risk allele 1 and 2 (1 stands for A or T and 2 stands for G or C) showed similar levels of endogenous DcR3 protein expression in whole cell lysates and supernatant. In comparison to control, the heterozygous patient (1/2) showed increased DcR3 protein levels in both whole cell lysates and supernatant. However, the non-secretor showed low endogenous DcR3 levels of protein in whole cell lysates with no detectable levels in supernatant, highlighting the secretion defect in human-derived EBV cells from IBD patients and controls, we described previously in transfected 293T cells.

Decoy Receptor 3 Induces Rapid Activation of Nuclear Factor Kappa B

Figure 2:
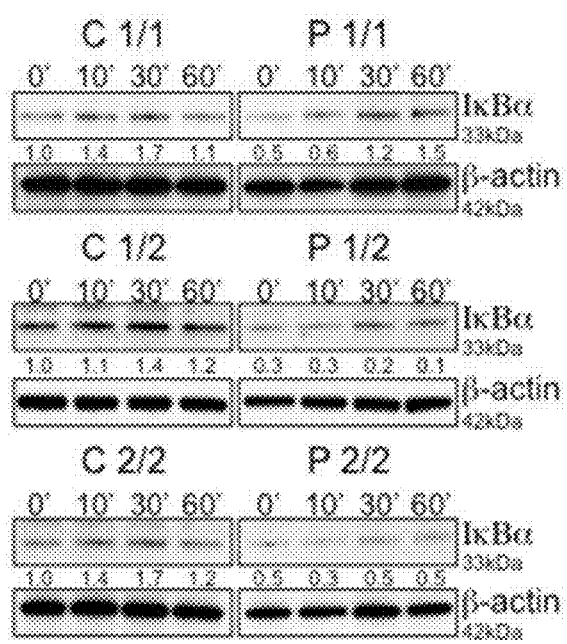
FIG. 2. Activation and kinetics of NF-κB was monitored by immunoblot analysis of IκBα in a time course experiment. Lysates of $10^6$ cells activated with TNF-α were separated by SDS-PAGE and evaluated for IκBα degradation in a time course experiment. Blots were stripped and reprobed for α-actin as a loading control. Numbers beneath each lane represent densitometric ratios of candidate protein normalized to the 0 minute time point.
Figure 3:
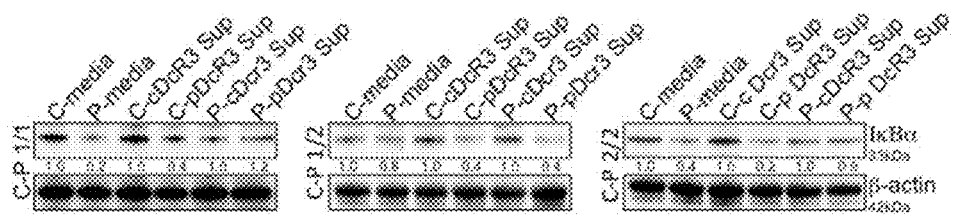
FIG. 3. Decoy receptor 3 (DcR3) induces the activation of NF-κB. Activation of NF-κB was monitored by immunoblot analysis of IκBα in control and patient cells with three different combinations of risk variants (1/1, 1/2 and 2/2). Cells were incubated with RPMI1640 medium (DMEM), control supernatant, and DcR3-containing supernatant for 30 min. Blots were stripped and reprobed for β-actin as a loading control; numbers beneath each lane represent densitometric ratios of candidate protein normalized to the loading control.

NF-κB is one of the key regulators in the immunological setting of IBD and therefore appears as a very promising target for therapeutic intervention in IBD. We next assessed whether having different combinations of risk variants results in differential DcR3 induced NF-κB activation, which in turn, differentially impacts its functions. We initially evaluated the kinetics of IκBα degradation in these cell lines activated with TNF-α for times ranging from 0 min to 60 min. As shown in FIG. 2, in comparison to controls patient homozygous for risk variant allele 1 showed early maximum IκBα degradation by 30 min. However, the patient with risk allele variant homozygous (2/2) and heterozygous (1/2) showed extended IκBα degradation up to 60 min. To further confirm that this activity was restricted specifically to patient cells, control and patient cells from each group were subjected to treatment of RPMI medium, control supernatant, DcR3-containing supernatant and vice versa for 60 min. In all the cases short-term treatment of control cells with DcR3 supernatants from patients resulted in a substantial degradation of IκBα, indicative of NF-κB activation (FIG. 3).

Figure 4:
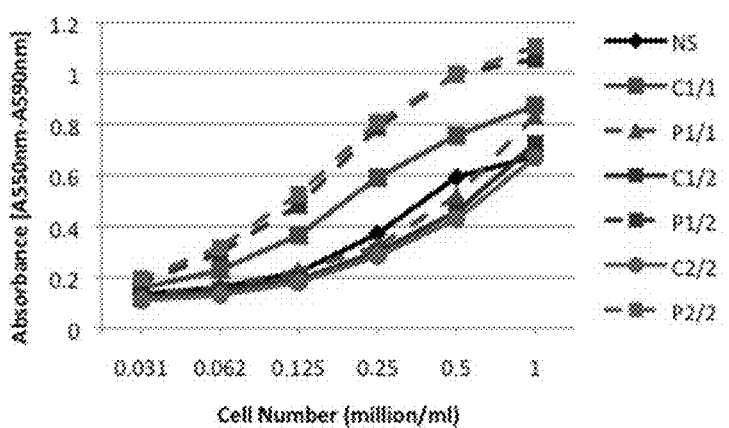
FIG. 4. MTT analysis. The cell proliferation was measured using an MTT (Microtiter-tetrazolium) based assay in non-secretor (●), control (■) and patient cells (▲) with three different combinations of risk variants (1/1, 1/2 and 2/2). The data is representative of five separate experiments.

We next investigated whether the presence of risk allele variants is associated with differential effects on cell proliferation. Control and patient cells with three different combinations of risk variants (1/1, 1/2 and 2/2) and non-secretor cells were subjected to MTT proliferation assay. The patient cells with 1/2 heterozygous and 2/2 homozygous risk alleles exhibited maximum proliferation in comparison to controls. Non-secretors exhibited lower rate of proliferation (FIG. 4). These data indicate that having different combinations of risk variants differentially alters functions mediated by DcR3.

Functional Relevance of DcR3 in Chronic Intestinal Inflammation

Figure 5A:
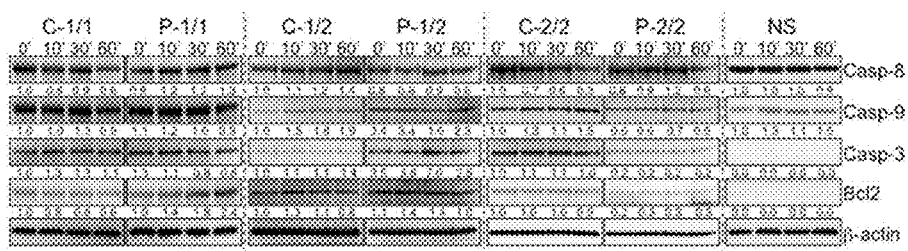
FIGS. 5A and 5B. Detection of Caspase-8, Caspase-3, Caspase-9 and Bcl-2.
Figure 5B:
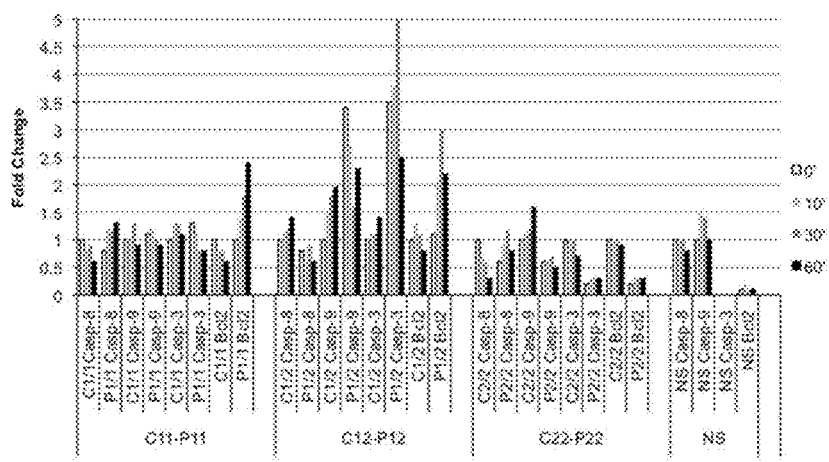

Considering that apoptosis plays a central role in regulation of tissue homeostasis, the imbalance between cell death and proliferation in favor of cell survival could result in chronic intestinal inflammation. We next investigated the differential effect of having risk allele variant of DcR3 on the extrinsic and intrinsic cell apoptosis pathway and cell survival. Western blot analysis was performed for protein expressions of caspase-8/9/3 and anti-apoptotic Bcl-2 on whole cell lysates of non-secretors, control and patient EBV transformed cells activated with TNF-α in a time course experiment, ranging from 0 min to 60 min (FIG. 5A). Patient cells with homozygous risk allele 1 exhibit no difference in caspase-8, 9 and 3 levels in comparison with control cells; however, they exhibit high anti-apoptotic Bcl2 protein levels. The patient EBV cells with heterozygous risk allele (1/2) exhibits high levels of capase-9 and 3 and high levels of anti-apoptotic Bcl2 protein levels in comparison with control cells. The patient EBV cells harboring homozygous risk allele 2 showed decreased levels of caspase 8, 9, 3 and low levels of anti-apoptotic Bcl2 protein in comparison with control cells. However, the non-secretors showed only caspase 8 and 9 with no detectable levels of caspase 3 and low levels of anti-apoptotic Bcl2 over the time course as depicted in bar graph (FIG. 5B). These data imply that the presence of different combinations of DcR3 risk variants give rise to differential regulation and activation of cell death and survival functions.

Role of NF-κB in IBD

Figure 6A:
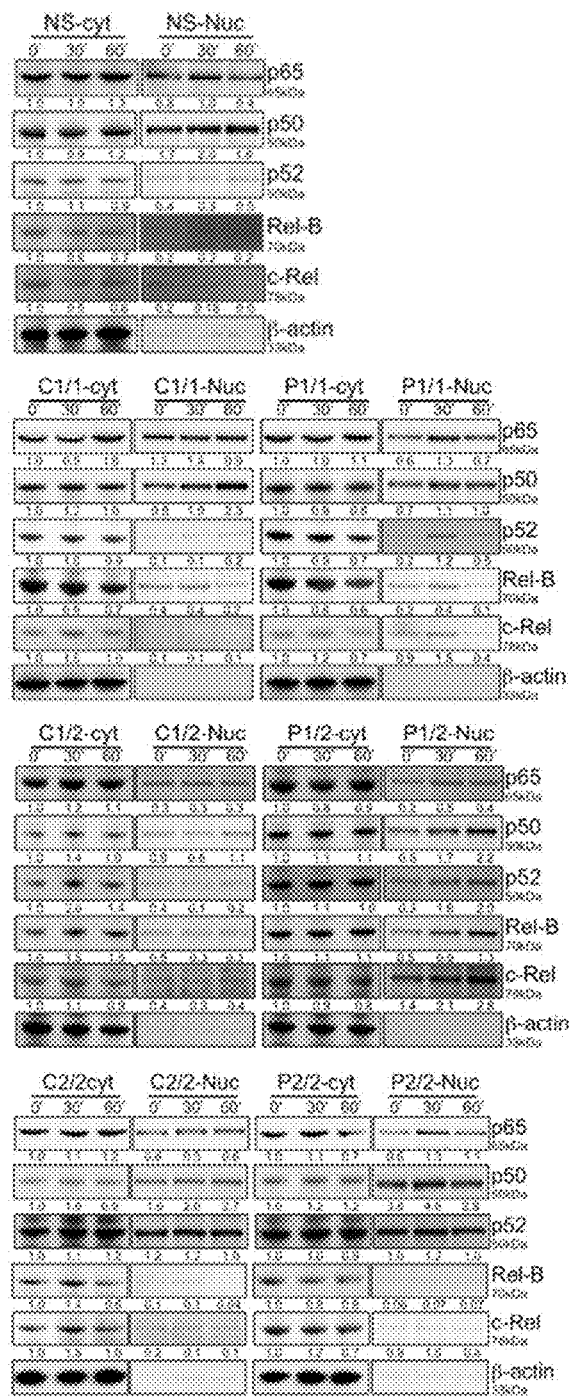
FIGS. 6A and 6B. Cytoplasmic and nuclear expression levels of specific NF-κB members.
Figure 6B:
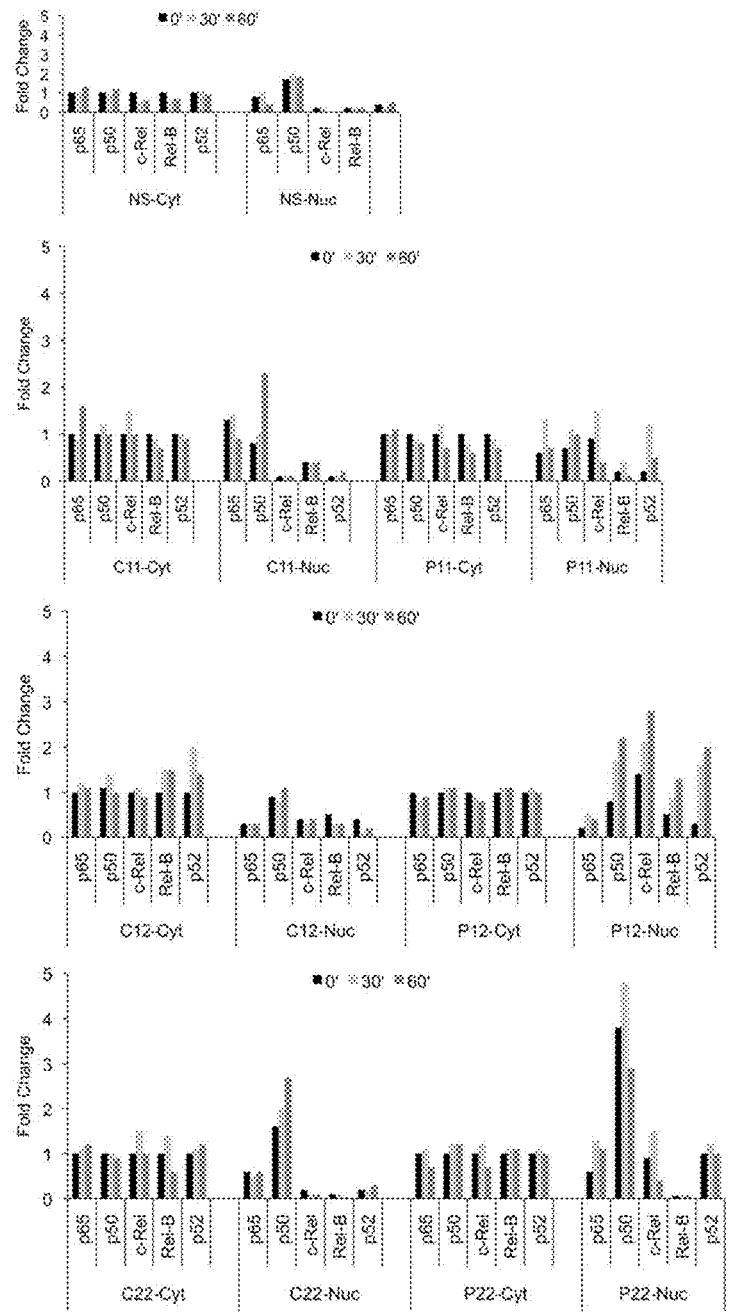

Although NF-κB is one of the key regulators in the immunological setting of IBD and therefore appears as a very promising target for therapeutic intervention in IBD, it is nevertheless important to remember that NF-κB is also involved in normal cell physiology. We next investigated the effects associated with the presence of risk allele variants of DcR3 in the context of NF-κB modulation. The NF-κB family of transcription factors contains five members, RelA (p65), RelB, c-Rel, NF-kB1 (p50), and NF-kB2 (p52). The existence of diversity among these proteins has raised the possibility that specific functions can be induced by particular hetero-dimers or homo-dimers in response to distinct stimuli. The most typical are hetero-dimers consisting of p65 (RelA) and p50 or c-Rel. Because little is known about the specific paradigm of NF-κB activation and the role that individual NF-κB family members may play in pathogenesis of human IBD, we wanted to understand the basic physiology of activation and expression pattern of NF-κB complexes in non-secretors, control and patient-derived EBV transformed cell lines. To determine whether enhanced expression and localization of NF-κB components is also detectable in the pediatric IBD patients, the cytoplasm as well as nuclear extracts was prepared from non-secretors, control and patient transformed EBV cell lines. The presence and precise nuclear translocation of different NF-κB family members was determined by western blot in a time course experiment from cells activated with TNF-α (FIGS. 6A & B). β-actin is included as a control for cytoplasmic extracts and also confirms the actin-poor nuclear fraction. Patient cells with homozygous risk allele 1 exhibit increased nuclear localization of c-Rel, p52 (non-classical component) and similar levels of classical heterodimers p65 and p50 in comparison with control cells. Another important finding is the existence of members of both classical and the non-classical NF-κB pathway in the nucleus of patient EBV cells with heterozygous risk allele (1/2). The patient EBV cells with heterozygous risk allele (1/2) exhibit relatively high nuclear levels of p50, c-Rel, RelB and p52 and similar levels of p65 in comparison with control cells. The patient EBV cells harboring homozygous risk allele 2 show high levels of p50 and similar levels of p65 and p52 in comparison with control cells. However, the non-secretors showed only the members of Classical NF-κB pathway in the nucleus. In addition, p50 is preferentially concentrated in the nucleus of all resting control and patient EBV cells irrespective of their allelic background and would be consistent with the existence of nuclear p50 homodimers that have been previously described to serve an inhibitory role (21, 22). These data suggest that having different combinations of DcR3 risk variant differentially regulates expression and localization of NF-κB family members.

siRNA Knockdown of DcR3 Expression

Figure 7A:
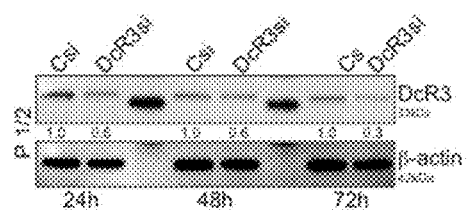
FIGS. 7A, 7B and 7C. siRNA knockdown of DcR3 expression.
Figure 7B:
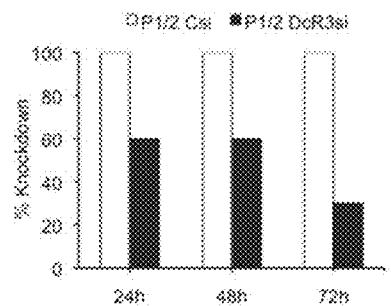
Figure 7C:
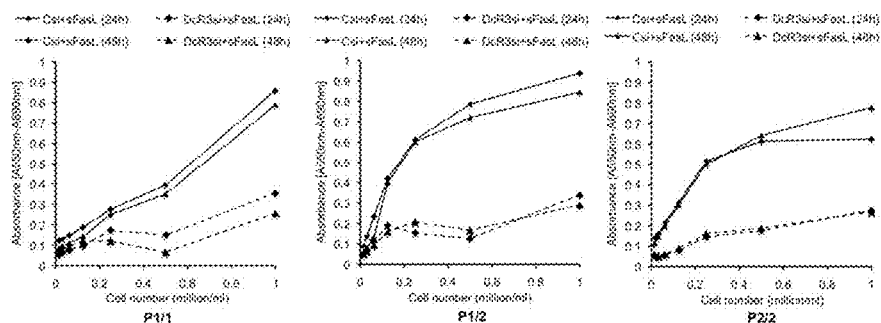

Previous studies have demonstrated that DcR3 acts as a decoy receptor and neutralizes the FasL-mediated apoptotic signal (1, 4). Since the patient EBV cells with heterozygous risk allele (1/2) exhibit more aggressive inflammatory marker upregulation in our experimental model, we next examined whether these EBV cells are benefitted from knockdown of DcR3 expression. FIGS. 7A & B shows the decrease in DcR3 expression post nucleofection of P (1/2) EBV cells with control siRNA and DcR3 siRNA. Post 24, 48 and 72 hours of nucleofection, cells were harvested and whole cell lysates were evaluated for DcR3 expression by immunoblot analysis. Blot shows reduced DcR3 levels first seen at 24 h and maintained for at least 48 h. Nucleofection had no adverse effect on cell viability (data not shown). In addition, cells nucleofected with control and DcR3 siRNA post 24 h were treated with sFasL and analysed for cell death using MTT Proliferation assay. Cells receiving DcR3 siRNA treated with sFasL showed decrease in cell growth in comparison to cells receiving the CsiRNA and sFasL (FIG. 7C). These results indicatet that siRNA knockdown of DcR3 expression ameliorates FasL-induced cytotoxic effects.

Discussion

Data in this example show that patients harboring risk variants in the TNFRSF6B gene exhibit differential pattern of DcR3 expression and NF-κB activation. The data also indicate that patients harboring risk variants in other genes in the DcR3 network may show a similarly differential pattern of DcR3 expression and NF-κB activation.

Control and patients harboring the homozygous for risk allele 1 or 2 (1 stands for A or T and 2 stands for G or C) show similar levels of endogenous DcR3 protein expression in whole cell lysates and supernatant. In comparison with controls, cells from the heterozygous patients (1/2) show increased DcR3 protein levels in both whole cell lysates and supernatant. Thus, risk variant carrier status impacts cellular levels of DcR3. We also obtained evidence that different combinations of risk variants affect DcR3 NF-κB activation inducing activity differentially, thereby functionally impacting this signaling pathway. In comparison with controls, cells from patients homozygous for risk variant allele 1 show early maximum IκBα degradation by 30 min. However, patients who are either homozygous (2/2) or heterozygous (1/2) for the risk allele showed extended IκBα degradation up to 6 mins and this DcR3 mediated rapid NF-κB activation activity was restricted specifically to patient cells harboring the risk variants.

The above results prompted us to investigate the effect of risk alleles at the DcR3 locus on the extrinsic and intrinsic cell apoptosis pathway and cell survival as a functional correlate. Binding of CD95L to CD95 initiates the extrinsic apoptosis pathway (11). Patient cells with homozygous risk allele 1 exhibit no difference in caspase-8, 9 and 3 levels in comparison with control cells, however they exhibit high anti-apoptotic Bcl2 protein levels. The patient EBV cells with heterozygous risk alleles (1/2) exhibit high levels of capase-9 and 3 and high levels of anti-apoptotic Bcl2 protein levels in comparison with control cells. The patient EBV cells harboring homozygous risk allele 2 showed decreased levels of caspase 8, 9, 3 and low levels of anti-apoptotic Bcl2 protein in comparison to control cells. In contrast, the non-secretors showed only caspase 8 and 9 with no detectable levels of caspase 3 and low levels of anti-apoptotic Bcl2 over time course. These data suggest that different combinations of DcR3 risk variants differentially regulate and activate cell death and survival functions.

Because little is known about the specific paradigm and considering the different cell-type specific effects which are mediated by NF-κB, we wanted to understand the basic physiology of activation and expression pattern of NF-κB complexes in non-secretors, including both controls and patient-derived EBV transformed cells. Patient cells with homozygous risk allele 1 showed increased nuclear localization of c-Rel, p52 (non-classical component) and similar levels of classical heterodimers p65 and p50 in comparison with control cells.

Another important finding is the existence of both classical and non-classical NF-kB pathway members in the nucleus of patient EBV cells with heterozygous risk allele (1/2). The patient EBV cells with heterozygous risk allele (1/2) exhibit relatively high nuclear levels of p50, c-Rel, RelB and p52 and similar levels of p65 in comparison with control cells. The patient EBV cells harboring homozygous risk allele 2 show high levels of p50 and similar levels of p65 and p52 in comparison with control cells. Though, the non-secretors exhibit deficiency of DcR3 expression, secretion, or ligand-binding, presence of members of Classical NF-κB pathway in the nucleus may lead to unopposed inflammatory signals and exacerbation of IBD and suggests that DcR3 may be less effective in down-regulating ligands that provoke inflammation in the IBD cases (6, 8, 12). In addition, p50 is preferentially concentrated in the nucleus of all resting control and patient EBV cells irrespective of their allelic background and would be consistent with the existence of nuclear p50 homodimers that have been previously described to serve an inhibitory role. Thus, increased processing of p105 and rapid degradation of IκBα by immunoproteasomes in CD patients may be responsible for enhanced expression of inflammatory genes regulated by p50/c-Rel and p50/p65 heterodimers. While previous studies suggest that NF-KB p65 is involved in the pathogenesis of CD, our data show that the abundance and mechanism of induction differs between individuals with different combinations of DcR3 risk variants. Most NF-κB inhibitors on the market and in development target only the better-known NF-kappa B canonical pathway. Our results indicate that the DcR3 is capable of inducing both canonical and non-canonical NF-κB pathways and the lesser-known non-canonical pathway actually may play a more important role in disease progression and pathogenesis. Many upstream signaling processes induce their activation through only one of the two pathways: the canonical or non-canonical (13). Most efforts to develop drugs that block NF-κB activation have focused on the canonical pathway because its targets—such as tumor necrosis factor (TNF) alpha—are better understood and easier to inhibit. But growing body of evidence shows the non-canonical pathway may play a more important role in disease. Rel-MD chose multiple myeloma (MM) as the lead indication based on a pair of studies reported by the Dana-Farber Cancer Institute. One study showed that an off-target effect of Velcade bortezomib was to induce up-regulation of the canonical pathway in MM cell lines and tumors (14). The other study showed that inhibiting both NF-kB activation pathways in MM cell lines was more effective than targeting just one (15). Thus, the non-canonical pathway may play a more important role in the development of new therapies in the future.

Conclusion

Taken together, we have investigated the immuno-modulatory role of DcR3 in EBV transformed cell lines from patients with and without risk variants in TNFRSF6B. EBV transformed cell lines derived from IBD patients harboring a risk variant in TNFRSF6B (such as the A allele of the rs2315008 SNP) exhibit differential patterns of DcR3 expression and NF-κB kinetics in comparison with wild type and promote inflammation in Crohn's disease by inhibiting FasL-induced apoptosis. siRNA-mediated knockdown post 24 hrs of nucleofection resulted in decreased DcR3 expression, increased cell death and decreased cell proliferation, effects that were also genotype-dependent. Our results offer first experimental evidence of involvement of non-canonical NF-κB signaling in pathogenesis of CD. We propose that pathogenic inflammation in CD is partially the result of non-canonical developmental signals impinging on a NF-κB signaling module with an altered homeostasis of I-κB proteins. Our findings establish that the non-canonical NF-κB pathway is a key player in the pathogenesis of IBD and provides new avenues for interventions targeting the DcR3 network genes through the development of new therapies.

References

1. Shih D Q, Targan S R. Insights into IBD Pathogenesis. Curr Gastroenterol Rep. 2009; 11:473-480
2. Kaser A, Zeissig S, Blumberg R S. Genes and environment: how will our concepts on the pathophysiology of IBD develop in the future? Dig Dis. 28:395-405
3. Denson L A, Long M D, McGovern D P, et al. Challenges in IBD research: update on progress and prioritization of the CCFA's research agenda. Inflamm Bowel Dis. 19:677-682
4. Kugathasan S, Baldassano R N, Bradfield J P, et al. Loci on 20q13 and 21q22 are associated with pediatric-onset inflammatory bowel disease. Nat Genet. 2008; 40:1211-1215
5. Franke A, McGovern D P, Barrett J C, et al. Genome-wide meta-analysis increases to 71 the number of confirmed Crohn's disease susceptibility loci. Nat Genet. 42:1118-1125
6. Lin W W, Hsieh S L. Decoy receptor 3: a pleiotropic immunomodulator and biomarker for inflammatory diseases, autoimmune diseases and cancer. Biochem Pharmacol. 81:838-847
7. Li H, Zhang L, Lou H, et al. Overexpression of decoy receptor 3 in precancerous lesions and adenocarcinoma of the esophagus. Am J Clin Pathol. 2005; 124:282-287
8. Kim S, Fotiadu A, Kotoula V. Increased expression of soluble decoy receptor 3 in acutely inflamed intestinal epithelia. Clin Immunol. 2005; 115:286-294
9. Neurath M F, Pettersson S, Meyer zum Buschenfelde K H, et al. Local administration of antisense phosphorothioate oligonucleotides to the p65 subunit of NF-kappa B abrogates established experimental colitis in mice. Nat Med. 1996; 2:998-1004
10. Neurath M F, Duchmann R, Meyer zum Buschenfelde K H. [Cytokines in chronic inflammatory intestinal diseases]. Dtsch Med Wochenschr. 1996; 121:735-741
11. Jin Z, El-Deiry W S. Overview of cell death signaling pathways. Cancer Biol Ther. 2005; 4:139-163
12. Wortinger M A, Foley J W, Larocque P, et al. Fas ligand-induced murine pulmonary inflammation is reduced by a stable decoy receptor 3 analogue. Immunology. 2003; 110:225-233
13. Hayden M S, Ghosh S. N F-kappaB in immunobiology. Cell Res. 21:223-244
14. Hideshima T, Ikeda H, Chauhan D, et al. Bortezomib induces canonical nuclear factor-kappaB activation in multiple myeloma cells. Blood. 2009; 114:1046-1052
15. Fabre C, Mimura N, Bobb K, et al. Dual inhibition of canonical and noncanonical NF-kappaB pathways demonstrates significant antitumor activities in multiple myeloma. Clin Cancer Res. 18:4669-4681

Example II

GWAS Study Data Concerning TNFRSF6B Genetic Alterations and Several Pediatric Autoimmune Diseases A link between genetic alteration in TNFRSF6B and inflammatory bowel disease (IBD) was initially found as part of a genome-wide association study (GWAS) conducted at the Children's Hospital of Philadelphia (CHOP). (See WO 2009/105590.) Correlations between TL1A (TNFSF15) genetic alterations and IBD were also observed in that study. A further GWAS analysis has now identified a link between genetic alteration in TNFRSF6B and further autoimmune diseases (AIDs) such as multiple sclerosis (MS), thryroiditis, and psoriasis. An aim of that further study was to identify genetic alterations genome-wide that correlate to incidence of AIDs in pediatric subjects (pAIDs).

The study was performed on a combined cohort of over 6035 pediatric cases across 10 clinically distinct pAIDs and 10718 population-based control subjects. Whole chromosome phasing was performed and the 1000 Genomes Project Phase I integrated cosmopolitan reference panel was used for imputation as described in Howie, B. et al. *Nat. Genet.* 44: 955-9 (2008) and Delaneau, O. et al. *BMC Bioinformatics* 9: 540 (2008). The study included only individuals with a self-reported European ancestry. Whole genome case-control association testing was performed using case samples from each of the 10 pAIDs selected and the shared controls. Additive logistic regression was applied using SNPTESTv2.5. There was no evidence of genomic inflation. To identify shared pAID association loci, an inverse chi-square meta-analysis was performed, accounting for sample size variation and the use of a shared control across the 10 pAIDs.

Among the loci identified in the study was TNFRSF6B, through the SNP rs2738774 at 20q13.33. Genetic alterations in this SNP were significantly correlated with several pAIDs including thyroiditis, psoriasis, systemic lupus erythematosus, ulcerative colitis, Crohn's disease, and juvenile idiopathic arthritis.

Further details of the study and the results associated with TNFRSF6B and other genes are provided in U.S. Provisional Appl. No. 62/208,383, filed Aug. 21, 2015, which is incorporated herein by reference and to which this application claims priority. See, e.g., supplemental Table 2A of that application.

Example III

Identification of Further DCR3 Network Genetic Alterations in IBD Subjects

Further GWAS data in pediatric IBD sufferers has also revealed genetic alterations (specifically, SNPs) in several DcR3 network genes that are enriched at least 2-fold in IBD cases compared to controls.

The following provides a table of such SNPs:

| SNP | CHR | BP | A1 | Freq cases | A2 | Func. Category | Gene | Function | rsID |
|---|---|---|---|---|---|---|---|---|---|
| 1:6525592 | 1 | 6525592 | T | 0.02 | C | exonic | TNFRSF25 | nonsynonymous_SNV | rs35771371 |
| 6:31540556 | 6 | 31540556 | C | 0.308 | T | exonic | LTA | nonsynonymous_SNV | rs2229094 |
| 6:31540757 | 6 | 31540757 | C | 0.072 | A | exonic | LTA | nonsynonymous_SNV | rs2229092 |
| 6:31544562 | 6 | 31544562 | T | 0.004 | C | exonic | TNF | nonsynonymous_SNV | rs4645843 |
| 6:31549357 | 6 | 31549357 | A | 0.004 | G | exonic | LTB | nonsynonymous_SNV | rs4647187 |
| 6:31549407 | 6 | 31549407 | T | 0.004 | C | exonic | LTB | nonsynonymous_SNV | rs3093554 |
| 10:90768676 | 10 | 90768676 | T | 0.008 | C | exonic | FAS | nonsynonymous_SNV | rs3218614 |

-continued

| SNP | CHR | BP | A1 | Freq cases | A2 | Func. Category | Gene | Function | rsID |
|---|---|---|---|---|---|---|---|---|---|
| 10:90771767 | 10 | 90771767 | A | 0.004 | G | exonic | FAS | nonsynonymous_SNV | rs56006128 |
| 19:6665020 | 19 | 6665020 | T | 0.048 | C | exonic | TNFSF14 | nonsynonymous_SNV | rs344560 |
| 19:6670070 | 19 | 6670070 | A | 0.004 | C | exonic | TNFSF14 | nonsynonymous_SNV | rs143389888 |
| 20:62328491 | 20 | 62328491 | T | 0.004 | G | exonic | TNFRSF6B | nonsynonymous_SNV | • |
| 20:62329644 | 20 | 62329644 | G | 0.004 | T | exonic | TNFRSF6B | nonsynonymous_SNV | • |

The following table provides a further set of mutations in TNFRSF6B that have been found to be enriched at least 2-fold in pediatric IBD sufferers compared to control subjects:

| SNP | BP | A1 | F_A | F_U | A2 | OR | Gene | Function | rsID |
|---|---|---|---|---|---|---|---|---|---|
| 20:62293235 | 62293235 | A | 0.004 | 0 | G | NA | TNFRSF6B | nonsynonymous_SNV | rs151214675 |
| 20:62304060 | 62304060 | C | 0.024 | 0.008734 | G | 2.089 | TNFRSF6B | • | rs7260740 |
| 20:62304061 | 62304061 | T | 0.024 | 0.008772 | G | 2.089 | TNFRSF6B | • | rs7260741 |
| 20:62309441 | 62309441 | A | 0.004 | 0 | C | NA | TNFRSF6B | • | rs183246776 |
| 20:62309514 | 62309514 | A | 0.028 | 0.008197 | G | 3.584 | TNFRSF6B | synonymous_SNV | rs41302954 |
| 20:62316772 | 62316772 | A | 0.008 | 0.002049 | G | 2.682 | TNFRSF6B | • | rs189434871 |
| 20:62317109 | 62317109 | T | 0.008 | 0 | C | NA | TNFRSF6B | • | rs375052586 |
| 20:62321073 | 62321073 | T | 0.044 | 0.0124 | C | 4.565 | TNFRSF6B | • | rs143200080 |
| 20:62321128 | 62321128 | A | 0.016 | 0.006173 | G | 2.45 | TNFRSF6B | nonsynonymous_SNV | rs35640778 |
| 20:62324328 | 62324328 | C | 0.004 | 0.002049 | G | 2.053 | TNFRSF6B | nonsynonymous_SNV | rs61736614 |
| 20:62324391 | 62324391 | A | 0.004 | 0.02049 | G | 0.1762 | TNFRSF6B | • | rs41308092 |
| 20:62324404 | 62324404 | T | 0.052 | 0.02049 | C | 3.067 | TNFRSF6B | • | rs117238689 |
| 20:62324416 | 62324416 | A | 0.004 | 0 | G | NA | TNFRSF6B | • | rs41308090 |
| 20:62324542 | 62324542 | C | 0.008 | 0 | G | NA | TNFRSF6B | nonsynonymous_SNV | rs115464632 |
| 20:62324673 | 62324673 | T | 0.004 | 0.00211 | C | 2 | TNFRSF6B | • | rs139133112 |
| 20:62326113 | 62326113 | C | 0.004 | 0 | A | NA | TNFRSF6B | synonymous_SNV | • |
| 20:62326159 | 62326159 | A | 0.004 | 0 | G | NA | TNFRSF6B | nonsynonymous_SNV | rs115303435 |
| 20:62326361 | 62326361 | C | 0.016 | 0.008197 | G | 2.839 | TNFRSF6B | • | rs182518802 |
| 20:62326498 | 62326498 | A | 0.004 | 0.002049 | G | 3.514 | TNFRSF6B | synonymous_SNV | rs41306796 |
| 20:62326566 | 62326566 | T | 0.004 | 0 | C | NA | TNFRSF6B | nonsynonymous_SNV | • |
| 20:62326874 | 62326874 | A | 0.004 | 0 | G | NA | TNFRSF6B | synonymous_SNV | rs181080831 |
| 20:62328491 | 62328491 | T | 0.004 | 0 | G | NA | TNFRSF6B | nonsynonymous_SNV | • |
| 20:62328587 | 62328587 | A | 0.004 | 0 | G | NA | TNFRSF6B | • | rs375269966 |
| 20:62328603 | 62328603 | G | 0.108 | 0 | T | NA | TNFRSF6B | • | • |
| 20:62328721 | 62328721 | G | 0.004 | 0 | A | NA | TNFRSF6B | synonymous_SNV | rs41304826 |
| 20:62329644 | 62329644 | G | 0.004 | 0 | T | NA | TNFRSF6B | nonsynonymous_SNV | • |
| 20:62331933 | 62331933 | A | 0.004 | 0.002075 | G | 495.1 | TNFRSF6B | • | rs7267337 |

Example IV

Screening Assays for Identifying Efficacious Therapeutics for the Treatment of Autoimmune Diseases The information herein above can be applied clinically to patients for diagnosing an AID or an increased susceptibility for developing one or more autoimmune diseases (AIDs) associated with altered DcR3 secretion and therapeutic intervention. Diagnostic compositions, including microarrays, and methods can be designed to identify the SNPs described herein in nucleic acids from a patient to assess susceptibility for developing an AID. This can occur after a patient arrives in the clinic; the patient has blood drawn, and using the diagnostic methods described herein, a clinician can detect a single nucleotide polymorphism as described in Example I. The information obtained from the patient sample, which can optionally be amplified prior to assessment, is used to diagnose a patient with an increased or decreased susceptibility for developing an AID. Kits for performing the diagnostic method of the invention are also provided herein. Such kits can comprise a microarray comprising at least one of the SNPs provided herein in and the necessary reagents for assessing the patient samples as described above. Alternatively, or in addition, the kits may comprise the reagents necessary to perform PCR to increase the level of signal in the sample.

The identity of AID-associated genes and the patient results will indicate which variants are present, and will identify those that have, or possess an altered risk for developing an AID. The information provided herein allows for therapeutic intervention at earlier times in disease progression than previously possible. Also as described herein above, the affected DcR3 gene is shown to associate with AIDs at genome wide significance levels, and thus provides a novel target for the development of new therapeutic agents efficacious for the treatment of these autoimmune disorders.

Example V

Test and Treat Method for Ameliorating Symptoms Associated with an Aid

In order to treat an individual having an AID, to alleviate a sign or symptom of the disease, suitable agents targeting the genes disclosed in the tables herein can be administered in combination in order to provide therapeutic benefit to the patient. Such agents should be administered in an effective dose.

First, a biological sample, or genotyping information may be obtained from a patient. Genetic information gleaned from nucleic acids present in the sample may be then assessed for the presence or absence of an AID-associated SNP containing nucleic acids associated with onset of one or more AID. The presence of these SNPs indicating the presence of an AID, along with the simultaneous identification of the gene(s) affected, may provide the clinician with guidance as to which therapeutic agents are appropriate. The total treatment dose or doses (when two or more targets are to be modulated) can be administered to a subject as a single dose or can be administered using a fractionated treatment protocol, in which multiple/separate doses are administered over a more prolonged period of time, for example, over the period of a day to allow administration of a daily dosage or over a longer period of time to administer a dose over a desired period of time.

In an individual suffering from an AID, in particular a more severe form of the disease, administration of AID therapeutic agents can be particularly useful when administered in combination, for example, with a conventional agent for treating such a disease. The skilled artisan can administer AID therapeutic agent(s), alone or in combination and can monitor the effectiveness of such treatment using routine methods such as pulmonary, bowel, thryroid, inflammatory function determination, radiologic, immunologic assays, or, where indicated, histopathologic methods.

The following table provides the sequences referred to in this application.

| SEQ ID NO | DESCRIPTION | SEQUENCE | | | |
|---|---|---|---|---|---|
| 1 | Human DcR3 amino acid sequence | MRALEGPGLS AETGERLVCA FWNYLERCRY AHAGFCLEHA SSSSSEQCQP LSTRVPGAEE GWGPTPRAGR RVARMPGLER | LLCLVLALPA QCPPGTFVQR CNVLCGEREE SCPPGAGVIA HRNCTALGLA CERAVIDFVA AALQLKLRRR SVRERFLPVH | LLPVPAVRGV PCRRDSPTTC EARACHATHN PGTPSQNTQC LNVPGSSSHD FQDISIKRLQ LTELLGAQDG | AETPTYPWRD GPCPPRHYTQ RACRCRTGFF QPCPPGTFSA TLCTSCTGFP RLLQALEAPE ALLVRLLQAL |
| 2 | Heavy Chain (HC) CDR1 antibody F19 | GYNWH | | | |
| 3 | HC CDR2 antibody F19 | EITHSGSTNYNPSLKS | | | |
| 4 | HC CDR3 antibody F19 | EIAVAGTGYYGMDV | | | |
| 5 | LC CDR1 antibody F19 | RASQGINSAFA | | | |
| 6 | LC CDR2 antibody F19 | DASSLES | | | |
| 7 | LC CDR3 antibody F19 | QQFNSYPLT | | | |
| 8 | Heavy chain variable region antibody F19 | QVQLQQWGAG PGKGLEWIGE KLSSVTAADT SSASTKGPSV VSWNSGALTS KTYTCNVDHK SVFLFPPKPK VDGVEVHNAK YKCKVSNKGL TKNQVSLTCL DSDGSFFLYS | LLKPSETLSL ITHSGSTNYN AVYYCVREIA FPLAPCSRST GVHTFPAVLQ PSNTKVDKRV DTLMISRTPE TKPREEQFNS PSSIEKTISK VKGFYPSDIA RLTVDKSRWQ | TCAVYGGSFS PSLKSRVTIS VAGTGYYGMD SESTAALGCL SSGLYSLSSV ESKYGPPCPP VTCVVVDVSQ TYRVVSVLTV AKGQPREPQV VEWESNGQPE EGNVFSCSVM | GYNWHWIRQP VDTSKNQFSL VWGQGTTVTV VKDYFPEPVT VTVPSSSLGT CPAPEFEGGP EDPEVQFNWY LHQDWLNGKE YTLPPSQEEM NNYKTTPPVL HEALHNHYTQ KSLSLSLG |
| 9 | Light chain variable region antibody F19 | AIQLTQSPSS GKAPKLLIYD EDFATYYCQQ SDEQLKSGTA ESVTEQDSKD LSSPVTKSFN | LSASVGDRVT ASSLESGVPS FNSYPLTFGG SVVCLLNNFY STYSLSSTLT RGEC | ITCRASQGIN RFSGSGSGTD GTKVEIKRTV PREAKVQWKV LSKADYEKHK | SAFAWYQQKP FTLTISSLQP AAPSVFIFPP DNALQSGNSQ VYACEVTHQG |
| 10 | Alternative LC CDR1 antibody F19 | RASRGINSAFA | | | |

-continued

| SEQ ID NO | DESCRIPTION | SEQUENCE |
|---|---|---|
| 11 | Alternative LC CDR2 antibody F19 | DASSLES |
| 12 | Alternative LC CDR3 antibody F19 | QQFNSYPLT |
| 13 | Alternative LC CDR1 antibody F19 | RVSQGISSYLN |
| 14 | Alternative LC CDR2 antibody F19 | SASNLQS |
| 15 | Alternative LC CDR3 antibody F19 | ARTNAPPT |
| 16 | Alternative LC CDR1 antibody F19 | RMSQGISSYLA |
| 17 | Alternative LC CDR2 antibody F19 | AASTLQS |
| 18 | Alternative LC CDR3 antibody F19 | QQYYSFPYT |
| 19 | Alternative LC CDR1 antibody F19 | RASQGVSSYLA |
| 20 | Alternative LC CDR2 antibody F19 | DASNRAT |
| 21 | Alternative LC CDR3 antibody F19 | QQRSNWHP |
| 22 | HC CDR1 antibody E1 | RFNMN |
| 23 | HC CDR2 antibody E1 | YISSSSYTIYYADSVKG |
| 24 | HC CDR3 antibody E1 | SIAAFDY |
| 25 | LC CDR1 antibody E1 | RASQGISSALA |
| 26 | LC CDR2 antibody E1 | DASSLES |
| 27 | LC CDR3 antibody E1 | QQFNSYRT |

-continued

| SEQ ID NO | DESCRIPTION | SEQUENCE |
|---|---|---|
| 28 | Alternative LC CDR1 antibody E1 | RASQSVSSSYLT |
| 29 | Alternative LC CDR2 antibody E1 | GASSRAT |
| 30 | Alternative LC CDR3 antibody E1 | QQYGSSMYT |
| 31 | Alternative LC CDR1 antibody E1 | RASQSVSSSYLA |
| 32 | Alternative LC CDR2 antibody E1 | GASNRAT |
| 33 | Alternative LC CDR3 antibody E1 | QQYGSSPWT |
| 34 | HC CDR1 antibody E13 | NAWMS |
| 35 | HC CDR2 antibody E13 | RIKSKIDGGTTDYAAPVKG |
| 36 | HC CDR3 antibody E13 | AMAGAFGF |
| 37 | LC CDR1 antibody E13 | RASQSVSSSYLA |
| 38 | LC CDR2 antibody E13 | GASSRAT |
| 39 | LC CDR3 antibody E13 | QQYGSSPMYT |
| 40 | HC CDR1 antibody E63 | SGGYYWS |
| 41 | HC CDR2 antibody E63 | YIYYSGSTNYNPSLKS |
| 42 | HC CDR3 antibody E63 | WITMFRGVGFDP |
| 43 | LC CDR1 antibody E63 | RASQSIGSSLH |
| 44 | LC CDR2 antibody E63 | YASQSFS |
| 45 | LC CDR3 antibody E63 | RQSSSLPLT |
| 46 | HC CDR1 antibody F23 | GYYWN |

-continued

| SEQ ID NO | DESCRIPTION | SEQUENCE |
|---|---|---|
| 47 | HC CDR2 antibody F23 | EINQYNPSLKS |
| 48 | HC CDR3 antibody F23 | EIAIADKGYYGLDV |
| 49 | LC CDR1 antibody F23 | RASQGISSALA |
| 50 | LC CDR2 antibody F23 | DASSLES |
| 51 | LC CDR3 antibody F23 | QQFNSYPLT |
| 52 | HC CDR1 | SYYIH |
| 53 | HC CDR2 | PGSDITKYNEKFKG |
| 54 | HC CDR3 | GISTYSAMDF |
| 55 | LC CDR1 | KASQDVGTAVA |
| 56 | LC CDR2 | WASTRHT |
| 57 | LC CDR3 | QQYSSYPLT |
| 58 | HC variable region | QVQLVQSGAE VKKPGASVKV SCKASGYTFT SYYIHWVRQA PGQRLEWMGW IFPGSDITKY NEKFKGRVTI TRDTSASTAY MELSSLRSED TAVYYCARED YGISTYSAMD FWGQGTLVTV SS |
| 59 | LC variable region | DIQLTQSPSF LSASVGDRVT ITCKASQDVG TAVAWYQQKP GKAPKLLIYW ASTRHTGVPS RFSGSGSGTE FTLTISSLQP EDFATYYCQQ YSSYPLTFGQ GTKVEIKR |
| 60 | HC CDR1 of 18E04 | HFDIN |
| 61 | HC CDR2 of 18E04 | WMNPDSDNTDYAQEFQG |
| 62 | HC CDR3 of 18E04 | GGTTLDY |
| 63 | LC CDR1 of 18E04 | SGDALPKKYAY |
| 64 | LC CDR2 of 18E04 | EDSKRPS |
| 65 | LC CDR3 of 18E04 | YSTDSSDNHVI |
| 66 | HC CDR1 of 98C07 | DYYMS |
| 67 | HC CDR2 of 98C07 | YISRSSFIYYSESVKG |
| 68 | HC CDR3 of 98C07 | WELSPFDY |
| 69 | LC CDR1 of 98C07 | RASQGISNYLA |
| 70 | LC CDR2 of 98C07 | AASSLQS |
| 71 | LC CDR3 of 98C07 | QQYNTYPFT |

| SEQ ID NO | DESCRIPTION | SEQUENCE |
|---|---|---|
| 72 | HC CDR1 of 1C02 | YYGIS |
| 73 | HC CDR2 of 1C02 | WISANSGNTNYAQKFQG |
| 74 | HC CDR3 of 1C02 | GGVAVLEY |
| 75 | LC CDR1 of 1C02 | WASQGISSYLA |
| 76 | LC CDR2 of 1C02 | VASTLQS |
| 77 | LC CDR3 of 1C02 | QQLKIYPLT |
| 78 | HC CDR1 of 1C06 | DYYMN |
| 79 | HC CDR2 of 1C06 | DISSRDNTIYYADSVKG |
| 80 | HC CDR3 of 1C06 | ARERGEGDYFGMDV |
| 81 | LC CDR1 of 1C06 | RASQDISSALA |
| 82 | LC CDR2 of 1C06 | DASSLES |
| 83 | LC CDR3 of 1C06 | QQFNTYPLT |

What is claimed is:

1. A method of treating ulcerative colitis (UC) or Crohn's disease (CD) in a patient in need thereof, comprising:
   (a) detecting the presence of at least one single nucleotide variation (SNV) in TNFRSF6B in a sample from the patient selected from
   A at rs151214675;
   C at rs7260740;
   T at rs7260741;
   A at rs183246776;
   A at rs41302954;
   A at rs189434871;
   T at rs375052586;
   T at rs143200080;
   A at rs35640778;
   C at rs61736614;
   G at rs41308092;
   T at rs117238689;
   A at rs41308090;
   C at rs115464632;
   T at rs139133112;
   A at rs115303435;
   C at rs182518802;
   A at rs41306796;
   A at rs181080831;
   A at rs375269966;
   G at rs41304826; and
   G to A at rs7267337; and
   (b) administering to the patient harboring the at least one SNV in TNFRSF6B an effective amount of an anti-LIGHT antibody, thereby treating UC or CD in the patient.

2. The method of claim 1, wherein the at least one SNV in TNFRSF6B is associated with reduced DcR3 level or activity.

3. The method of claim 1, further comprising detecting the presence of at least one SNV selected from
   a SNV in TNFRSF25 consisting of a T at rs35771371;
   a SNV in LTA consisting of a C at rs2229094;
   a SNV in LTA consisting of a C at rs2229092;
   a SNV in TNF consisting of a T at rs4645843;
   a SNV in LTB consisting of a A at rs4647187;

a SNV in LTB consisting of a T at rs3093554;
a SNV in FAS consisting of a T at rs3218614;
a SNV in FAS consisting of a A at rs56006128;
a SNV in TNFSF14 consisting of a T at rs344560; and
a SNV in TNFSF14 consisting of a A at rs143389888.

4. The method of claim 3, further comprising assessing each of DcR3, DR3, TL1A, LIGHT, FasL, HVEM, LTA, LTB, FasR(CD95), and LIGHT receptor genes for the presence of a SNV.

5. The method of claim 1, wherein the patient is a pediatric patient.

6. The method of claim 1, wherein the anti-LIGHT antibody comprises a heavy chain and a light chain that together comprise a set of complementary determining region (CDR)-H1, CDR-H2, CDR-H3, CDR-L1, CDR-L2, and CDR-L3 comprising the amino acid sequences of SEQ ID NOs: 2, 3, 4, 5, 6, and 7.

7. The method of claim 6, wherein the anti-LIGHT antibody comprises heavy and light chain variable regions at least 95% identity to SEQ ID NOs: 8 and 9 or SEQ ID NOs: 58 and 59.

8. The method of claim 7, wherein the anti-LIGHT antibody comprises heavy and light chain variable regions comprising the amino acid sequences of SEQ ID NOS: 8 and 9.

9. The method of claim 1, wherein said detecting is performed via at least one of in situ hybridization, Southern hybridization, quantitative polymerase chain reaction (PCR), droplet PCR, TaqMan probe hybridization, fluorescent in situ hybridization (FISH), Single Nucleotide Variation (SNV)/Single Nucleotide Polymorphism (SNP) genotyping, comparative genomic hybridization, whole genome sequencing, and whole exome sequencing.

10. The method of claim 1, further comprising detection of a C at rs2738774.

11. A method of treating ulcerative colitis (UC) or Crohn's disease (CD) in a patient in need thereof, comprising determining the patient has at least one single nucleotide variation (SNV) in TNFRSF6B selected from A at rs151214675;
C at rs7260740;
T at rs7260741;
A at rs183246776;
A at rs41302954;
A at rs189434871;
T at rs375052586;
T at rs143200080;
A at rs35640778;
C at rs61736614;
G at rs41308092;
T at rs117238689;
A at rs41308090;
C at rs115464632;
T at rs139133112;
A at rs115303435;
C at rs182518802;
A at rs41306796;
A at rs181080831;
A at rs375269966;
G at rs41304826; and
A at rs7267337;
and administering an effective amount of an anti-LIGHT antibody to the patient.

12. The method of claim 11, wherein the patient is a pediatric patient.

13. The method of claim 11, wherein the anti-LIGHT antibody comprises a heavy chain and a light chain that together comprise a set of complementary determining region (CDR)-H1, CDR-H2, CDR-H3, CDR-L1, CDR-L2, and CDR-L3 comprising the amino acid sequences of SEQ ID NOs: 2, 3, 4, 5, 6, and 7.

14. The method of claim 13, wherein the anti-LIGHT antibody comprises heavy and light chain variable regions with at least 95% identity to SEQ ID NOs: 8 and 9.

15. The method of claim 14, wherein the anti-LIGHT antibody comprises heavy and light chain variable regions comprising the sequences of SEQ ID NOS: 8 and 9.

16. The method of claim 11, further comprising detection of a C at rs2738774.

* * * * *